(12) United States Patent
Yim et al.

(10) Patent No.: US 10,957,013 B2
(45) Date of Patent: Mar. 23, 2021

(54) METHOD AND APPARATUS FOR SYNTHESIZING MEDICAL IMAGES

(71) Applicant: SAMSUNG ELECTRONICS CO., LTD., Suwon-si (KR)

(72) Inventors: Jin-woo Yim, Seongnam-si (KR); Ho-kyung Kang, Seoul (KR); Ki-won Sohn, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/953,531

(22) Filed: Nov. 30, 2015

(65) Prior Publication Data
US 2016/0335742 A1    Nov. 17, 2016

(30) Foreign Application Priority Data

May 15, 2015    (KR) .................. 10-2015-0068187

(51) Int. Cl.
*G06K 9/00* (2006.01)
*G06T 3/40* (2006.01)
(Continued)

(52) U.S. Cl.
CPC ............ *G06T 3/4038* (2013.01); *A61B 6/032* (2013.01); *A61B 6/5288* (2013.01); *A61B 8/085* (2013.01); *A61B 8/0891* (2013.01); *A61B 8/463* (2013.01); *A61B 8/483* (2013.01); *A61B 8/5207* (2013.01); *A61B 8/5253* (2013.01); *A61B 8/5276* (2013.01); *A61B 8/5284* (2013.01); *G01R 33/5608* (2013.01); *G01S 7/52065* (2013.01);
(Continued)

(58) Field of Classification Search
CPC ............ G06T 2207/10132; G06T 2207/10136
See application file for complete search history.

(56) References Cited

U.S. PATENT DOCUMENTS 5,251,628 A * 10/1993 Foo ..................... A61B 5/0456
600/413
5,278,652 A *  1/1994 Urbanus .............. G09G 3/2092
348/571
(Continued)

FOREIGN PATENT DOCUMENTS

CN    103006217 A    4/2013
CN    106163405 A    11/2016
(Continued)

OTHER PUBLICATIONS

Communication dated Sep. 16, 2016, issued by the European Patent Office in counterpart European application No. 16156252.5.
(Continued)

*Primary Examiner* — Avinash Yentrapati
(74) *Attorney, Agent, or Firm* — Sughrue Mion, PLLC

(57) ABSTRACT

A method of synthesizing medical images includes acquiring image data of an object; generating first medical image frames of the object based on the image data; selecting, from among the first medical image frames, second medical image frames corresponding to points of time that have the same electrocardiogram (ECG) signal information of the object; generating a panoramic image by synthesizing the second medical image frames; and displaying the panoramic image on a display.

15 Claims, 17 Drawing Sheets
(7 of 17 Drawing Sheet(s) Filed in Color)

(51) Int. Cl.

| | | |
|---|---|---|
| *A61B 6/03* | (2006.01) | |
| *A61B 6/00* | (2006.01) | |
| *A61B 8/08* | (2006.01) | |
| *A61B 8/00* | (2006.01) | |
| *H04N 5/232* | (2006.01) | |
| *G01S 15/89* | (2006.01) | |
| *G01R 33/56* | (2006.01) | |
| *G01S 7/52* | (2006.01) | |
| *G06T 11/00* | (2006.01) | |
| *G01R 33/567* | (2006.01) | |
| *A61B 5/055* | (2006.01) | |

(52) U.S. Cl.
  CPC ...... *G01S 7/52088* (2013.01); *G01S 15/8936* (2013.01); *G06T 11/008* (2013.01); *H04N 5/23238* (2013.01); *A61B 5/055* (2013.01); *A61B 6/503* (2013.01); *A61B 6/504* (2013.01); *A61B 6/506* (2013.01); *A61B 6/5241* (2013.01); *A61B 6/5264* (2013.01); *A61B 8/0883* (2013.01); *A61B 8/467* (2013.01); *A61B 8/488* (2013.01); *G01R 33/5673* (2013.01); *G01S 15/8979* (2013.01); *G01S 15/8995* (2013.01); *G06T 2207/20212* (2013.01); *G06T 2207/30048* (2013.01)

(56) References Cited

U.S. PATENT DOCUMENTS

| | | | | |
|---|---|---|---|---|
| 5,690,111 A * | 11/1997 | Tsujino | A61B 5/0456 600/440 |
| 5,692,213 A * | 11/1997 | Goldberg | G06F 3/16 375/E7.271 |
| 5,782,766 A * | 7/1998 | Weng | G06T 7/246 128/916 |
| 5,993,390 A * | 11/1999 | Savord | A61B 8/08 128/916 |
| 5,999,173 A * | 12/1999 | Ubillos | G11B 27/034 348/E5.056 |
| 6,117,081 A * | 9/2000 | Jago | G01S 7/52025 600/443 |
| 6,159,152 A * | 12/2000 | Sumanaweera | A61B 8/14 600/443 |
| 6,266,553 B1 * | 7/2001 | Fluhrer | A61B 6/032 378/145 |
| 6,301,496 B1 * | 10/2001 | Reisfeld | A61B 5/04011 345/419 |
| 6,328,693 B1 * | 12/2001 | Miyatake | A61B 8/14 600/437 |
| 6,381,487 B1 * | 4/2002 | Flohr | A61B 6/4085 600/425 |
| 6,416,477 B1 * | 7/2002 | Jago | G01S 7/52065 600/447 |
| 6,484,048 B1 * | 11/2002 | Hoshino | G01R 33/4833 345/419 |
| 6,514,207 B2 * | 2/2003 | Ebadollahi | G06T 7/0012 348/E5.112 |
| 6,532,036 B1 * | 3/2003 | Peleg | G06T 3/4038 348/36 |
| 7,565,019 B2 * | 7/2009 | Dong | G06K 9/32 345/32 |
| 8,142,358 B2 * | 3/2012 | Pedrizzetti | A61B 8/463 600/450 |
| 8,880,352 B2 * | 11/2014 | Kale | A61B 5/04525 702/19 |
| 9,149,249 B2 * | 10/2015 | Matsunaga | A61B 8/4281 |
| 9,615,809 B2 | 4/2017 | Lee et al. | |
| 2002/0007117 A1 * | 1/2002 | Ebadollahi | G06T 7/0012 600/437 |
| 2002/0154173 A1 * | 10/2002 | Etgen | G06F 3/04855 715/833 |
| 2002/0168069 A1 * | 11/2002 | Tehranchi | G06T 1/005 380/235 |
| 2003/0016782 A1 * | 1/2003 | Kaufman | A61B 6/467 378/50 |
| 2003/0016851 A1 * | 1/2003 | Kaufman | A61B 6/032 382/131 |
| 2004/0236219 A1 * | 11/2004 | Liu | G01S 7/52079 600/437 |
| 2004/0249259 A1 * | 12/2004 | Heimdal | G01S 7/52087 600/407 |
| 2005/0107688 A1 * | 5/2005 | Strommer | A61F 2/95 600/424 |
| 2005/0154305 A1 * | 7/2005 | Kamiyama | G01S 7/52087 600/443 |
| 2005/0222506 A1 | 10/2005 | Takimoto et al. | |
| 2005/0272997 A1 * | 12/2005 | Grist | G01R 33/5673 600/410 |
| 2006/0262970 A1 * | 11/2006 | Boese | G06T 7/38 382/131 |
| 2007/0161895 A1 | 7/2007 | Kim et al. | |
| 2007/0167801 A1 * | 7/2007 | Webler | A61B 8/445 600/459 |
| 2008/0081987 A1 * | 4/2008 | Miyazaki | A61B 5/055 600/410 |
| 2008/0221442 A1 * | 9/2008 | Tolkowsky | A61B 6/541 600/425 |
| 2008/0304730 A1 * | 12/2008 | Abe | G06T 7/12 382/131 |
| 2009/0149749 A1 * | 6/2009 | Heron | A61B 8/0883 600/437 |
| 2009/0198134 A1 * | 8/2009 | Hashimoto | A61B 8/0883 600/443 |
| 2009/0262980 A1 * | 10/2009 | Markowitz | A61B 5/0422 382/103 |
| 2009/0279765 A1 * | 11/2009 | Qu | A61B 6/5211 382/132 |
| 2010/0022877 A1 | 1/2010 | Chono | |
| 2010/0027968 A1 * | 2/2010 | Bourdon | H04N 5/913 386/252 |
| 2010/0040193 A1 * | 2/2010 | Lessick | A61B 6/541 378/8 |
| 2010/0061611 A1 * | 3/2010 | Xu | G06T 7/136 382/131 |
| 2010/0168573 A1 * | 7/2010 | Sherrill | A61B 8/483 600/440 |
| 2010/0232665 A1 | 9/2010 | Amir | |
| 2010/0235746 A1 * | 9/2010 | Anzures | G11B 27/034 715/723 |
| 2011/0105902 A1 * | 5/2011 | Kume | G06T 7/215 600/443 |
| 2011/0164800 A1 * | 7/2011 | Kokubun | A61B 6/032 382/131 |
| 2012/0130245 A1 * | 5/2012 | Chono | A61B 8/0891 600/443 |
| 2013/0331700 A1 * | 12/2013 | Kawabata | A61B 8/14 600/443 |
| 2014/0100441 A1 * | 4/2014 | Jo | A61B 5/055 600/410 |
| 2014/0328462 A1 * | 11/2014 | Uehara | A61B 6/5288 378/62 |
| 2015/0085972 A1 * | 3/2015 | Choi | A61B 6/5288 378/8 |
| 2015/0131886 A1 * | 5/2015 | Aben | A61B 8/5261 382/132 |
| 2015/0223771 A1 * | 8/2015 | Lee | A61B 6/503 382/131 |
| 2015/0342571 A1 * | 12/2015 | Ohuchi | A61B 8/0883 382/128 |
| 2016/0171726 A1 * | 6/2016 | Nam | G06T 11/006 382/131 |
| 2018/0247437 A1 * | 8/2018 | Hoornaert | G06T 7/38 |

FOREIGN PATENT DOCUMENTS

| | | |
|---|---|---|
| DE | 19541987 A1 | 5/1996 |
| DE | 102011075287 A1 | 11/2012 |

(56) References Cited

FOREIGN PATENT DOCUMENTS

| EP | 2037413 A2 * | 3/2009 | ............ A61B 5/055 |
|---|---|---|---|
| JP | 9-75339 A | 3/1997 | |
| JP | 3410843 B2 | 5/2003 | |
| JP | 2004229958 A | 8/2004 | |
| JP | 2009-022459 A | 2/2009 | |
| JP | 2011-98016 A | 5/2011 | |
| KR | 10-2007-0074027 A | 7/2007 | |

OTHER PUBLICATIONS

Communications (PCT/ISA/220, 210, 237) dated Mar. 7, 2016, issued by the International Searching Authority in counterpart International Application No. PCT/KR2015/013006.
Communication dated Apr. 20, 2017, issued by the Korean Intellectual Property Office in counterpart Korean Application No. 10-2015-0068187.
Communication issued by the Korean Intellectual Property Office dated Oct. 27, 2017 in counterpart Korean Patent Application No. 10-2015-0068187.
Communication dated Dec. 30, 2019 issued by the State Intellectual Property Office of P.R. China in counterpart Chinese Application No. 201580080024.5.
Communication dated Jul. 24, 2020, from the State Intellectual Property Office of People's Republic of China in counterpart Application No. 201580080024.5.
Communication dated Oct. 10, 2018 issued by the European Patent Office in European Counterpart Application No. 16 156 252.5.
Machine Translation of JP 2009-022459 A, TXPJPEA / Clarivate Analytics, 2017, 33 total pages.

* cited by examiner

FIRST MEDICAL IMAGE FRAME

FIG. 13A
FIG. 13B
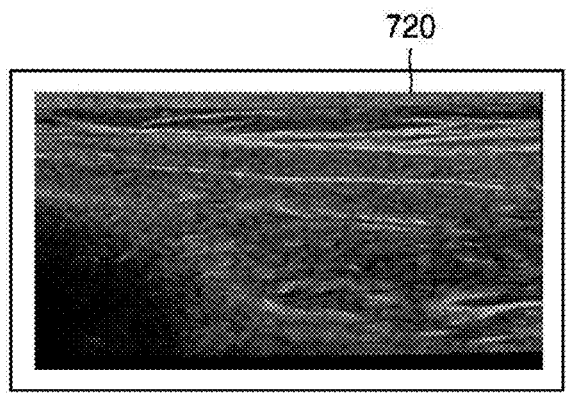
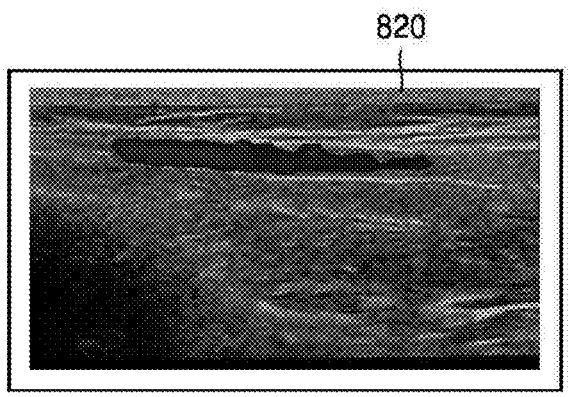

730

830

METHOD AND APPARATUS FOR SYNTHESIZING MEDICAL IMAGES

CROSS-REFERENCE TO RELATED APPLICATION

This application claims the benefit of Korean Patent Application No. 10-2015-0068187, filed on May 15, 2015, in the Korean Intellectual Property Office, the disclosure of which is incorporated herein in its entirety by reference.

BACKGROUND

1. Field

The exemplary embodiments relate to methods and apparatuses for synthesizing medical images in consideration of bio-signal information corresponding to a physical activity of an object, and more particularly, to methods and apparatuses for synthesizing medical images in consideration of electrocardiogram (ECG) signal information of an object.

2. Description of the Related Art

Ultrasound diagnostic apparatuses transmit ultrasound signals generated by transducers of a probe to an object and receive echo signals reflected from the object, thereby obtaining at least one image of an internal part of the object (e.g., soft tissues or blood flow). In particular, ultrasound diagnostic apparatuses are used for medical purposes including observation of the interior of an object, detection of foreign substances, and diagnosis of damage to the object. Such ultrasound diagnostic apparatuses provide high stability, display images in real time, and are safe due to the lack of radioactive exposure, compared to X-ray apparatuses. Therefore, ultrasound diagnostic apparatuses are widely used together with other image diagnostic apparatuses including a computed tomography (CT) apparatus, a magnetic resonance imaging (MRI) apparatus, and the like.

An ultrasound system provides panoramic images based on ultrasound images that are continuously obtained by moving an ultrasonic probe along a surface of an object. That is, the ultrasound system continuously obtains ultrasound images by moving the ultrasonic probe along the surface of the object and forms panoramic images by synthesizing the obtained ultrasound images.

SUMMARY

Exemplary embodiments disclosed herein provide methods and apparatuses for synthesizing medical images which may select only some of medical image frames that are continuously obtained, in consideration of bio-signal information corresponding to a physical activity of an object, and may synthesize panoramic images, thereby outputting the panoramic images with high accuracy.

Exemplary embodiments disclosed herein further provide methods and apparatuses for synthesizing medical images which may select some image frames corresponding to points of time that have the same electrocardiogram (ECG) signal information of an object from among medical image frames that are continuously obtained and may synthesize the selected image frames, thereby synthesizing panoramic images.

Additional aspects will be set forth in part in the description which follows and, in part, will be apparent from the description, or may be learned by practice of the presented exemplary embodiments.

According to an aspect of an exemplary embodiment, there is provided a method of synthesizing medical images, the method including: acquiring image data of an object; generating first medical image frames of the object based on the image data; selecting, from among the first medical image frames, second medical image frames corresponding to points of time that have the same electrocardiogram (ECG) signal information of the object; generating a panoramic image by synthesizing the second medical image frames; and displaying the panoramic image on a display.

The acquiring of the image data of the object includes: transmitting an ultrasound signal to the object and receiving a response signal based on the transmitted ultrasound signal; and acquiring the image data based on the received response signal.

The acquiring of the image data of the object includes: transmitting a radio frequency (RF) signal to the object and receiving a magnetic resonance (MR) signal that is emitted from the object based on the RF signal; and acquiring MR image data based on the received MR signal.

The acquiring of the image data of the object includes: transmitting an X-ray signal to the object and detecting the X-ray signal that is transmitted through the object; and acquiring computed tomography (CT) image data based on the detected X-ray signal.

The method may further include correlating ECG signal information of the object with the panoramic image to thereby generate correlated information and storing the correlated information, and displaying the correlated information together on the display.

The points of time that have the same ECG signal information are points of time that have the same singular points extracted from an ECG image.

The method may further include selecting, from among the first medical images, third medical image frames corresponding to points of time that have pieces of ECG signal information; generating panoramic image frames by synthesizing third medical image frames corresponding to points of time that have the same ECG signal information, among the second medical image frames; and continuously outputting the panoramic image frames to the display.

According to another aspect of an exemplary embodiment, there is provided an apparatus configured to synthesize medical images, the apparatus including: a data acquirer configured to acquire image data of an object; an image processor configured to generate first medical image frames that constitute a video of the object based on the image data, select, from among the first medical image frames, second medical image frames corresponding to points of time that have the same electrocardiogram (ECG) signal information of the object, and generate a panoramic image by synthesizing the second medical image frames; and a display configured to output the panoramic image.

The data acquirer may further include an ultrasound transceiver configured to transmit an ultrasound signal to the object, receive a response signal based on the ultrasound signal, and acquire ultrasound image data based on the response signal.

The data acquirer may be configured to transmit a radio frequency (RF) signal to the object, receive a magnetic resonance (MR) signal that is emitted from the object based on the RF signal, and acquire MR image data based on the MR signal.

The data acquirer may be configured to transmit an X-ray signal to the object, detect the X-ray signal that is transmitted through the object, and acquire computed tomography (CT) image data based on the detected X-ray signal.

The apparatus may further include a memory configured to correlate ECG signal information of the object with the panoramic image to thereby generate correlated information and store the correlated information, wherein the display is configured to display the correlated information together on the display.

The points of time that have the same ECG signal information are points of time that have the same singular points extracted from an ECG image.

The image processor may be configured to select, from among the first medical images, third medical image frames corresponding to points of time that have pieces of ECG signal information, and generate panoramic image frames by synthesizing third medical image frames corresponding to points of time that have the same ECG signal information from among the second medical image frames, and the display may be configured to continuously output the panoramic image frames.

According to another aspect of an exemplary embodiment, there is provided a non-transitory computer-readable storage medium having recorded thereon computer program codes for executing a method of synthesizing medical images, the codes being derived and executed by a processor, wherein the method includes: acquiring image data of an object; generating first medical image frames of the object based on the image data; selecting, from among the first medical image frames, second medical image frames corresponding to points of time that have the same electrocardiogram (ECG) signal information of the object; generating a panoramic image by synthesizing the second medical image frames; and displaying the panoramic image on a display.

The method may further include: selecting, from among the first medical image frames, third medical image frames corresponding to points of time that have pieces of ECG signal information; generating panoramic image frames by synthesizing third medical image frames corresponding to points of time that have the same ECG signal information among the second medical image frames; and continuously outputting the panoramic images to the display.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and/or other aspects will become apparent and more readily appreciated from the following description of the exemplary embodiments, taken in conjunction with the accompanying drawings in which:

FIGS. 11, 12, 13A, 13B, 14A and 14B are views illustrating various examples where the ultrasound diagnostic apparatus displays generated panoramic images, according to an exemplary embodiment.

DETAILED DESCRIPTION

Figure 1:
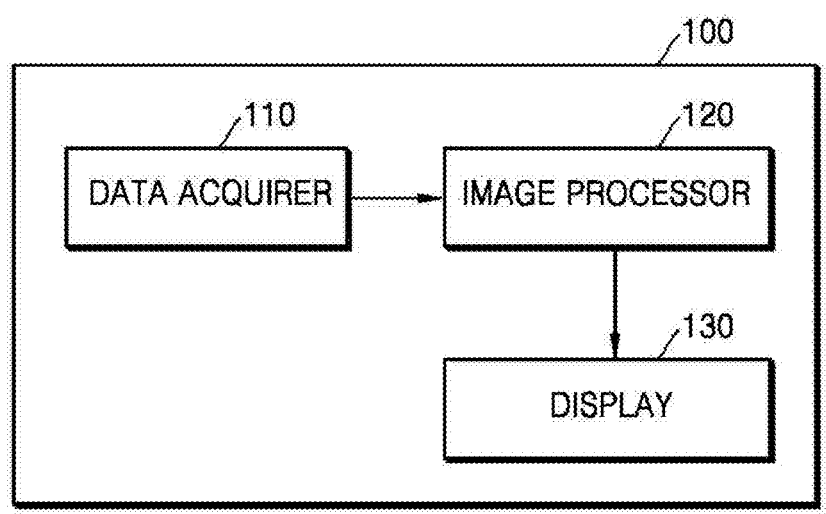
FIG. 1 is a block diagram illustrating a configuration of an apparatus for synthesizing images, according to an exemplary embodiment.

The terms used herein are those general terms currently widely used in the art in consideration of functions regarding the inventive concept, but the terms may vary according to the intention of one of ordinary skill in the art, precedents, or new technology in the art. Also, some terms may be arbitrarily selected by the applicant, and in this case, the meaning of the selected terms will be described in detail in the detailed description of the present specification. Thus, the terms used herein should be defined based on the meaning of the terms together with the description throughout the specification.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software.

As used herein, the term "and/or" includes any and all combinations of one or more of the correlated listed items. Expressions such as "at least one of" when preceding a list of elements, modify the entire list of elements and do not modify the individual elements of the list.

The term "image" used herein may refer to multi-dimensional data including discrete image elements (e.g., pixels for two-dimensional (2D) images and voxels for three-dimensional (3D) images). For example, the image may be, but is not limited to being, a medical image (e.g., an ultrasound image, a computed tomography (CT) image, or a magnetic resonance (MR) image) of an object that is obtained by an ultrasound apparatus, a CT apparatus, or a magnetic resonance imaging (MRI) apparatus.

The ultrasound image may refer to an image obtained by emitting an ultrasound signal, which is generated from a transducer of a probe, to the object and receiving information of an echo signal reflected from the object. Also, the ultrasound image may be formed in various ways. For example, the ultrasound image may be at least one of an amplitude (A)-mode image, a brightness (B)-mode image, a color (C)-mode image, and a Doppler (D)-mode image.

The CT image may refer to an image obtained by synthesizing a plurality of X-ray images that are obtained by taking a picture of the object through rotation about at least one axis of the object.

The MR image may refer to an image of the object that is obtained by using nuclear magnetic resonance (NMR).

Furthermore, the term "object" may refer to a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom refers to a material having a density, an effective atomic number, and a volume that are approximately the same as those of an organism. For example, the phantom may refer to a spherical phantom having properties similar to a human body.

Throughout the specification, the term "user" may refer to, but is not limited to referring to, a medical expert, for example, a medical doctor, a nurse, a medical laboratory technologist, or a medical imaging expert, or a technician who repairs medical apparatuses.

Hereinafter, exemplary embodiments will be described in detail with reference to the accompanying drawings.

FIG. 1 is a block diagram illustrating a configuration of an apparatus 100 for synthesizing medical images, according to an exemplary embodiment. The apparatus 100 may include a data acquirer 110, an image processor 120, and a display 130.

The data acquirer 110 may acquire image data of an object. For example, the data acquirer 110 may transmit an ultrasound signal to the object and may receive an echo signal reflected from the object. The data acquirer 110 may process the received echo signal and may generate ultrasound image data of the object.

Alternatively, the data acquirer 110 may transmit a radio frequency (RF) signal to the object and may receive an MR signal that is emitted from the object. The data acquirer 110 may process the received MR signal and may generate MR image data of the object.

Alternatively, the data acquirer 110 may transmit X-rays to the object and may detect an X-ray signal transmitted through the object. The data acquirer 110 may process the detected X-ray signal and may generate CT image data of the object.

Alternatively, the data acquirer 110 may receive image data that is generated by an ultrasound diagnostic apparatus, an MR apparatus, or a CT apparatus that is located outside the apparatus 100, without receiving an ultrasound signal, an MR signal, or an X-ray signal from the object and directly generating image data of the object.

The image processor 120 may generate a plurality of first medical image frames based on the image data that is received from the data acquirer 110. For example, the plurality of first medical image frames may be a plurality of image frames that are temporally adjacent to one another.

Also, the image processor 120 may generate a panoramic image based on the plurality of first medical image frames. The image processor 120 may generate the panoramic image by synthesizing second medical image frames that are selected based on bio-signal information of the object from among the first medical image frames. The bio-signal information of the object may include information related to a body movement corresponding to a physical activity of the object for a predetermined period of time for which the first medical image frames are generated. Also, the bio-signal information may be obtained from at least one medical image obtained by taking a picture of the body movement of the object. In this case, the at least one medical image may include, but is not limited to including, at least one of a blood vessel image, a musculoskeletal image, and an electrocardiogram (ECG) image.

The image processor 120 according to an exemplary embodiment may select second medical image frames corresponding to points of time that have the same ECG signal information of the object from among the plurality of first medical image frames and may generate a panoramic image by synthesizing only the second medical image frames.

The display 130 according to an exemplary embodiment may output the panoramic image that is generated by the image processor 120.

The display 130 according to an exemplary embodiment may output and display various pieces of information processed by the apparatus 100 as well as the panoramic image through a graphical user interface (GUI) onto a screen. The apparatus 100 may include two or more displays 130 according to a type of the apparatus 100.

Figure 2:
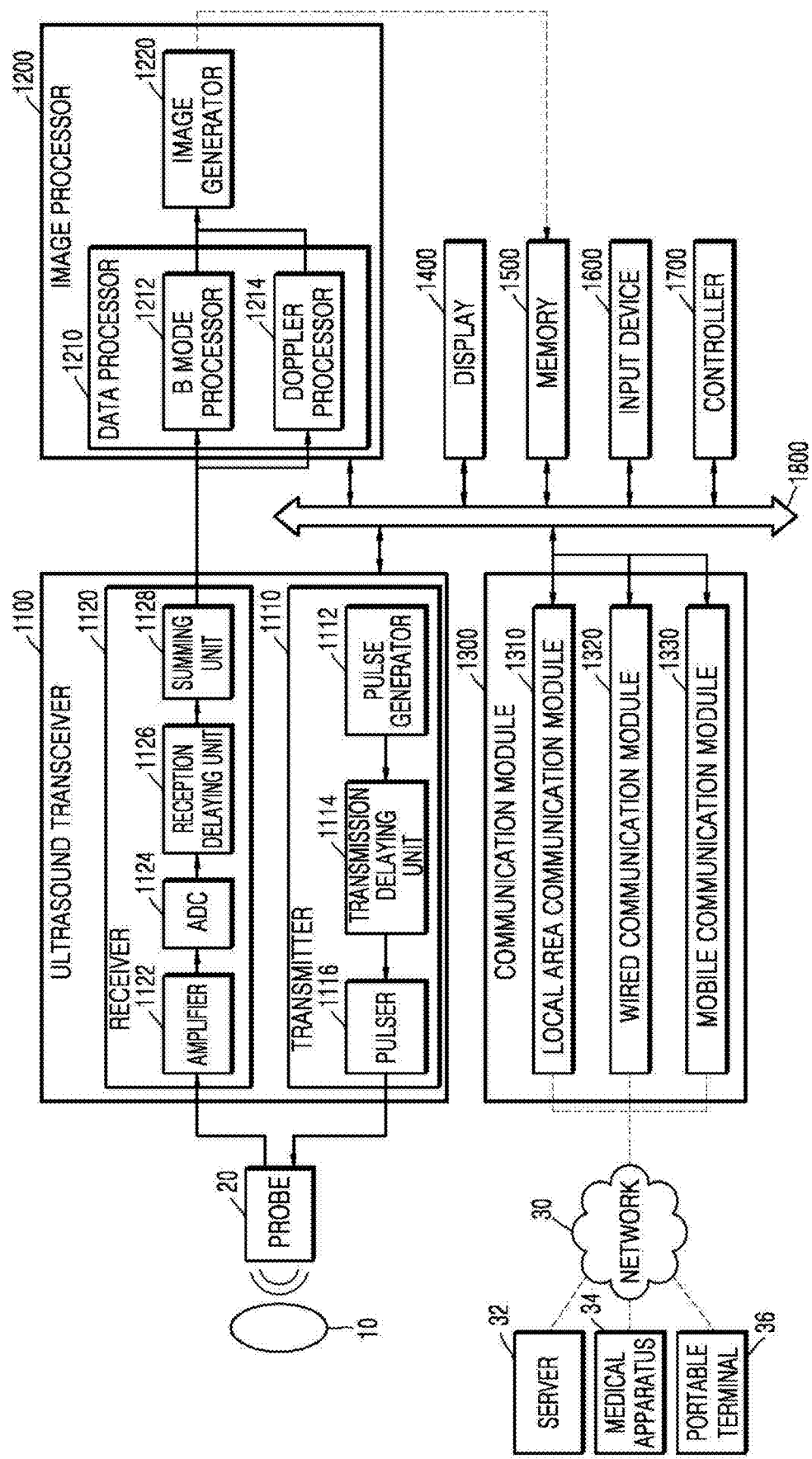
FIG. 2 is a block diagram illustrating a configuration of an apparatus for synthesizing images, according to an exemplary embodiment.

FIG. 2 is a block diagram illustrating a configuration of an apparatus 1000 for synthesizing medical images, according to an exemplary embodiment. Referring to FIG. 2, the apparatus 1000 may be an ultrasound diagnostic apparatus. The apparatus 1000 may include a probe 20, an ultrasound transceiver 1100, an image processor 1200, a communication module 1300 (e.g., communicator), a display 1400, a memory 1500, an input device 1600, and a controller 1700, which may be connected to one another via a bus 1800.

The data acquirer 110 of FIG. 1 may correspond to the ultrasound transceiver 1100 of FIG. 2, the image processor 120 of FIG. 1 may correspond to the image processor 1200 of FIG. 2, and the display 130 of FIG. 1 may correspond to the display 1400 of FIG. 2.

The apparatus 1000 may be a cart-type apparatus or a portable apparatus. Examples of portable ultrasound diagnostic apparatuses may include, but are not limited to including, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 1100 and receives echo signals reflected from the object 10. The probe 20 includes a plurality of transducers, and the plurality of transducers oscillate in response to electrical signals and generate acoustic energy, that is, ultrasound waves. Furthermore, the probe 20 may be connected to a main body of the apparatus 1000 by wire or wirelessly, and according to exemplary embodiments, the apparatus 1000 may include a plurality of the probes 20.

The probe 20 according to an exemplary embodiment may continuously transmit ultrasound signals to the object 10 while moving along a surface of the object 10 and may continuously receive echo signals reflected from the object 10.

A transmitter 1110 applies a driving signal to the probe 20. The transmitter 1110 includes a pulse generator 1112, a transmission delaying unit 1114 (e.g., transmission delayer), and a pulser 1116. The pulse generator 1112 generates pulses for forming transmission ultrasound waves based on a predetermined pulse repetition frequency (PRF), and the transmission delaying unit 1114 delays the pulses by delay times used for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 1120 may include an amplifier 1122, an analog-to-digital converter (ADC) 1124, a reception delaying unit 1126 (e.g., reception delayer), and a summing unit 1128 (e.g., summer). The amplifier 1122 amplifies echo signals in each channel, and the ADC 1124 performs analog-to-digital conversion with respect to the amplified echo signals. The reception delaying unit 1126 delays digital echo signals output by the ADC 1124 by delay times used for determining reception directionality, and the summing unit 1128 generates ultrasound data by summing the echo signals processed by the reception delaying unit 1166. In some exemplary embodiments, the receiver 1120 may not include the amplifier 1122. In other words, if the sensitivity of the probe 20 or the capability of the ADC 1124 to process bits is enhanced, the amplifier 1122 may be omitted.

The ultrasound transceiver 1100 according to an exemplary embodiment may generate ultrasound image data by continuously transmitting ultrasound signals to the object 10 and continuously receiving response signals to the transmitted ultrasound signals. The image processor 1200 generates an ultrasound image by scan-converting ultrasound data generated by the ultrasound transceiver 1100 and displays the ultrasound image. The ultrasound image may be not only a grayscale ultrasound image obtained by scanning the object 10 in an amplitude (A)-mode, a brightness (B)-mode, and a motion (M)-mode, but also a Doppler image showing a movement of the object 10 via a Doppler effect. The Doppler image may be a blood flow Doppler image showing the flow of blood (also referred to as a color Doppler image), a tissue Doppler image showing a movement of tissue, or a spectral Doppler image showing a moving speed of the object 10 as a waveform.

A B-mode processor 1212 extracts B-mode components from the ultrasound data and processes the B-mode components. An image generator 1220 may generate an ultrasound image indicating signal intensities as brightness based on the extracted B-mode components.

Similarly, a Doppler processor 1214 may extract Doppler components from the ultrasound data, and the image generator 1220 may generate a Doppler image indicating a movement of the object 10 as colors or waveforms based on the extracted Doppler components.

According to an exemplary embodiment, the image generator 1220 may generate a 3D ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

The image processor 1200 according to an exemplary embodiment may generate a plurality of first medical image frames based on the ultrasound image data that is received from the ultrasound transceiver 1100.

For example, the plurality of first medical image frames may be a plurality of image frames that are temporally adjacent to one another.

Also, the image processor 1200 according to an exemplary embodiment may generate a panoramic image based on the plurality of first medical image frames.

In particular, the image processor 1200 according to an exemplary embodiment may generate the panoramic image by synthesizing second medical image frames that are selected based on bio-signal information of the object 10 from among the first medical image frames. For example, the bio-signal information of the object 10 may include information related to a body movement corresponding to a physical activity of the object 10 during a predetermined period of time for which the first medical image frames are generated. According to exemplary embodiments, the process of synthesizing the second medical image frames may be performed according to many different synthesizing techniques, as would be appreciated by one of ordinary skill in the art. For example, the process of synthesizing according to an exemplary embodiment may employ various types of synthesis algorithms, although is not limited thereto.

In this case, the bio-signal information may be obtained from at least one medical image that is obtained by taking a picture of the body movement of the object 10. The at least one medical image according to an exemplary embodiment includes a medical image that is different from the first medical image frames.

For example, the bio-signal information of the object 10 may be directly obtained by the controller 1700 based on at least one medical image received from an apparatus for obtaining medical images.

Also, the bio-signal information may be directly obtained from the apparatus for obtaining medical images and may be received through the communication unit 1300.

For example, an apparatus for obtaining images (not shown) may be an apparatus that obtains medical images of the object 10. Examples of the apparatus for obtaining images (not shown) according to an exemplary embodiment may include, but are not limited to including, a CT apparatus, an MRI apparatus, an angiography apparatus, and an ultrasound apparatus.

Also, the apparatus for obtaining images may include a plurality of apparatuses for obtaining images, and may include different types of apparatuses for obtaining images using different image obtaining methods or the same type of apparatuses for obtaining images using the same image obtaining method.

For example, the at least one medical image may include at least one of a blood vessel image, a musculoskeletal image, and an ECG image, although is not limited thereto as long as the medical image is a medical image obtained by taking a picture of the body movement of the object 10.

The communication unit 1300 according to an exemplary embodiment may receive the at least one medical image obtained by taking a picture of the body movement of the object 10 from the apparatus for obtaining medical images through a network. Also, the communication unit 1300 according to an exemplary embodiment may directly obtain the bio-signal information from the apparatus for obtaining images.

For example, the image processor 1200 may select second medical image frames corresponding to points of time that have the same ECG signal information of the object 10 from the first medical image frames and may generate panoramic images by synthesizing only the second medical image frames.

The display 1400 displays the generated ultrasound image. The display 1400 may display not only the ultrasound image, but also various pieces of information processed by the apparatus 1000 on a screen through a GUI. In addition, the apparatus 1000 may include two or more displays 1400 according to exemplary embodiments.

The display 1400 according to an exemplary embodiment may output the panoramic images that are generated by the image processor 1200.

The communication unit 1300 is connected to a network 30 by wire or wirelessly to communicate with an external device or a server. The communication unit 1300 may exchange data with a hospital server or another medical apparatus in a hospital, which is connected thereto via a PACS. Furthermore, the communication unit 1300 may perform data communication according to the digital imaging and communications in medicine (DICOM) standard.

The communication unit 1300 may transmit or receive data related to diagnosis of the object 10, e.g., an ultrasound image, ultrasound data, and Doppler data of the object 10, via the network 30 and may also transmit or receive medical images captured by another medical apparatus, e.g., a CT apparatus, an MRI apparatus, or an X-ray apparatus. Furthermore, the communication unit 1300 may receive information about a diagnosis history or a medical treatment schedule of a patient from a server and utilizes the received information to diagnose the patient. Furthermore, the communication unit 1300 may perform data communication not only with a server or a medical apparatus in a hospital, but also with a portable terminal of a medical doctor or the patient.

The communication unit 1300 is connected to the network 30 by wire or wirelessly to exchange data with a server 32, a medical apparatus 34, or a portable terminal 36. The communication unit 1300 may include one or more components for communication with external devices. For example, the communication unit 1300 may include a local area communication module 1310 (e.g., local area communicator), a wired communication module 1320 (e.g., wired communicator), and a mobile communication module 1330 (e.g., mobile communicator).

The local area communication module 1310 refers to a module for local area communication within a predetermined distance. Examples of local area communication techniques according to an exemplary embodiment may include, but are not limited to including, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 refers to a module for communication using electrical signals or optical signals. Examples of wired communication techniques according to an exemplary embodiment may include communication via a twisted pair cable, a coaxial cable, an optical fiber cable, and an Ethernet cable.

The mobile communication module 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various types of data processed by the apparatus 1000. For example, the memory 1500 may store medical data related to diagnosis of the object 10, such as ultrasound data and an ultrasound image that are input or output, and may also store algorithms or programs which are to be executed in the apparatus 1000.

The memory 1500 may be any of various types of storage media, e.g., a flash memory, a hard disk drive, EEPROM, etc. Furthermore, the apparatus 1000 may utilize web storage or a cloud server that performs the storage function of the memory 1500 online.

The input device 1600 refers to a unit via which a user inputs data for controlling the apparatus 1000. The input device 1600 may include hardware components, such as a keypad, a mouse, a touch pad, a touch screen, and a jog switch. However, exemplary embodiments are not limited thereto, and the input device 1600 may further include any of various other types of input units including an ECG measuring module, a respiration measuring module, a voice recognition sensor, a gesture recognition sensor, a fingerprint recognition sensor, an iris recognition sensor, a depth sensor, a distance sensor, or any other type of sensor known to those skilled in the art.

The controller 1700 may control all operations of the apparatus 1000. In other words, the controller 1700 may control operations among the probe 20, the ultrasound transceiver 1100, the image processor 1200, the communication unit 1300, the display 1400, the memory 1500, and the input device 1600 shown in FIG. 1.

All or some of the probe 20, the ultrasound transceiver 1100, the image processor 1200, the communication unit 1300, the display 1400, the memory 1500, the input device 1600, and the controller 1700 may be implemented as software modules. Also, at least one of the ultrasound transceiver 1100, the image processor 1200, and the communication unit 1300 may be included in the controller 1600; however, the exemplary embodiments are not limited thereto.

Figure 3:
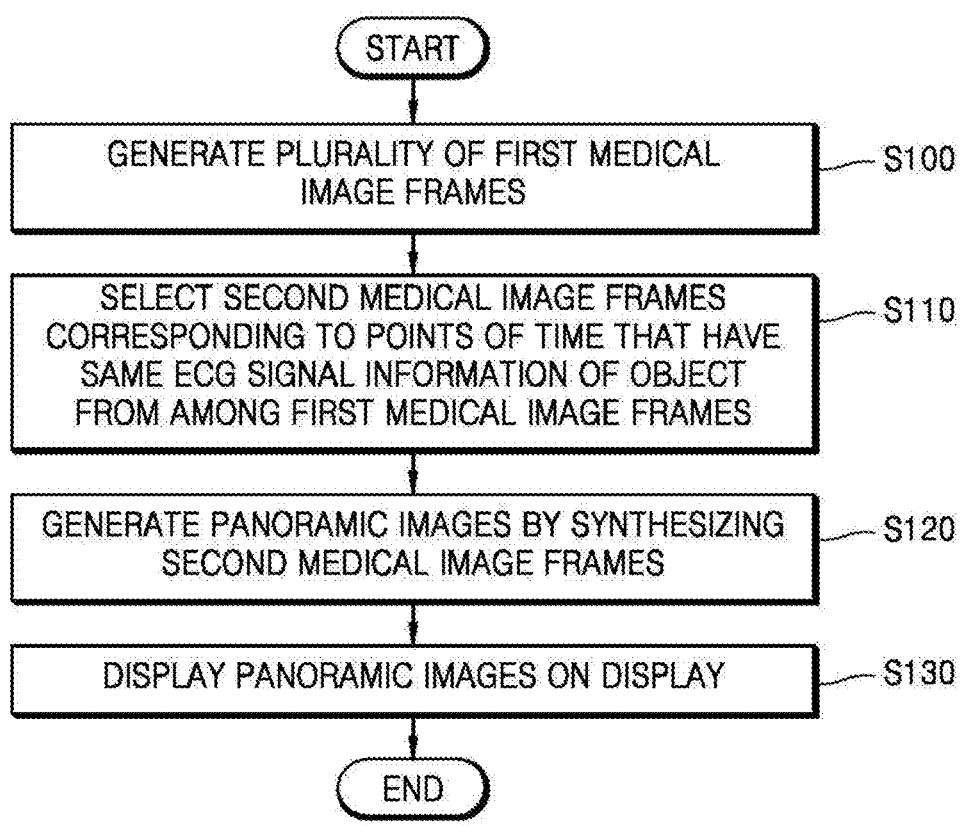
FIG. 3 is a flowchart of a method of synthesizing medical images to generate a panoramic image, according to an exemplary embodiment.

FIG. 3 is a flowchart of a method of synthesizing medical images to generate a panoramic image, according to an exemplary embodiment.

In operation S100, the apparatus 100 receives a plurality of first medical image frames.

The apparatus 100 may acquire image data of an object and may generate the plurality of first image frames based on the acquired image data.

For example, the apparatus 100 may transmit an ultrasound signal to the object and may generate the first image frames based on ultrasound image data that is acquired by receiving a response signal to the transmitted ultrasound signal.

Alternatively, the apparatus 100 may transmit an RF signal to the object and may receive an MR signal that is emitted from the object. The apparatus 100 may acquire MR image data of the object by processing the received MR signal and may generate the first image frames based on the acquired MR image data.

Alternatively, the apparatus 100 may transmit X-rays to the object and may detect an X-ray signal transmitted through the object. The apparatus 100 may acquire CT image data of the object by processing the detected X-ray signal and may generate the first medical image frames based on the acquired CT image data. Also, the plurality of first medical image frames that are image frames that are continuously acquired while the probe 20 moves along a surface of the object for a predetermined period of time may reflect a body movement related to a physical activity of the object that occurs during a medical procedure. For example, the plurality of first medical image frames that are temporally adjacent to one another may be obtained while ECG signal information of the object is obtained.

In operation S110, the apparatus 100 selects second medical image frames corresponding to points of time that have the same ECG signal information of the object from among the first medical image frames that are generated in operation S100.

An ultrasound diagnostic apparatus according to an exemplary embodiment may select the second medical image frames based on bio-signal information of the object from among the first medical image frames.

For example, the bio-signal information may be the body movement related to the physical activity of the object that occurs while the first medical image frames are generated. Also, the bio-signal information according to an exemplary embodiment may be a value that is previously determined before the medical procedure using the apparatus 1000 that is an ultrasound diagnostic apparatus.

For example, at least one medical image that is generated by an apparatus for acquiring medical images may be at least one medical image acquired by taking a picture of the body movement of the object before the apparatus 1000 generates the first medical image frames.

For example, the at least one medical image generated by the apparatus for acquiring medical images may include at least one of a blood vessel image, a musculoskeletal image, and an ECG image.

In this case, examples of the body movement related to the physical activity of the object may include, but are not limited to including, a change in a thickness of a blood vessel and a change in a muscle type according to a heartbeat of the object. The bio-signal information according to an exemplary embodiment that is time information corresponding to a cycle of the body movement of the object may be obtained based on the at least one medical image generated by the apparatus for obtaining medical images, instead of the first medical image frames according to an exemplary embodiment. Of course, it is understood that the body movement is not limited to the above examples, and may instead be many other types of body movements according to exemplary embodiments, such as other types of movements related to the circulatory system, other types of muscles, neural activities, or movements of other parts of the human body, e.g., other organs, bones, etc.

For example, the bio-signal information may include, but is not limited to including, at least one of a cycle of the heartbeat of the object, a cycle of the change in the thickness of the blood vessel, and a cycle of the change in the muscle type that are included in the at least one medical image.

Also, the bio-signal information according to an exemplary embodiment that is state information corresponding to the body movement of the object may be obtained based on the at least one medical image that is generated by the apparatus for obtaining medical images, instead of the first medical image frames according to an exemplary embodiment.

For example, the bio-signal information may include, but is not limited to including, at least one of a state of the heartbeat, a state of the thickness of the blood vessel, and a state of the muscle type of the object that are included in the at least one medical image.

The apparatus 1000 according to an exemplary embodiment may correlate the bio-signal information that is obtained based on a medical image that is previously generated before ultrasound imaging with the first medical image frames that are generated in real time during the ultrasound imaging.

For example, a periodic body movement of the object included in the first medical image frames may be derived from the bio-signal information that is previously determined.

When the body movement of the object included in the medical image is a periodic movement and time information corresponding to a cycle of the body movement of the object is T (sec), the apparatus 1000 according to an exemplary embodiment has to obtain the plurality of first medical image frames by using an imaging time of at least 2 T (sec).

The bio-signal information of the object according to an exemplary embodiment may include ECG signal information of the object, and the first medical image frames may be obtained while the ECG signal information of the object is generated. In this case, the first medical image frames that are generated in real time during ultrasound imaging may be correlated with the ECG signal information of the object that is obtained in real time during the ultrasound imaging. A method of correlating the first medical image frames with the ECG signal information of the object will be explained below in detail with reference to FIG. 7.

The second medical image frames according to an exemplary embodiment may be a plurality of image frames having the same bio-signal information among the first medical image frames.

In this case, the bio-signal information is information related to the body movement corresponding to the physical activity of the object. When two medical image frames have the same bio-signal information, this correlation may indicate that the body movements of the object included in the two medical image frames are the same.

Since a movement of the object included in the first medical image frames derived from the bio-signal information is periodic, medical image frames corresponding to points of time that have the same movements of the object exist in each cycle. Accordingly, only some medical image frames whose body movements correspond to predetermined points of time may be selected as the second medical image frames from among the plurality of first medical image frames.

Also, the second medical image frames according to another exemplary embodiment may be a plurality of image frames corresponding to a plurality of pieces of bio-signal information among the first medical image frames.

For example, the bio-signal information of the object includes ECG signal information of the object, and only second medical image frames corresponding to points of time that have the same ECG signal information of the object may be selected from among the first medical image frames, which will be explained below in detail with reference to FIGS. 4 and 10.

In operation S120, the apparatus 100 generates a panoramic image by synthesizing the second medical image frames that are selected in operation S110.

The panoramic image may be generated by synthesizing a plurality of second medical image frames having the same bio-signal information among the first medical image frames. For example, the bio-signal information may include ECG signal information, and the panoramic image may be generated by synthesizing only a plurality of second medical image frames corresponding to points of time that have the same ECG signal information of the object among the first medical image frames.

In operation S130, the apparatus 100 displays the panoramic image that is generated in operation S120 on the display 1400.

Figure 4:
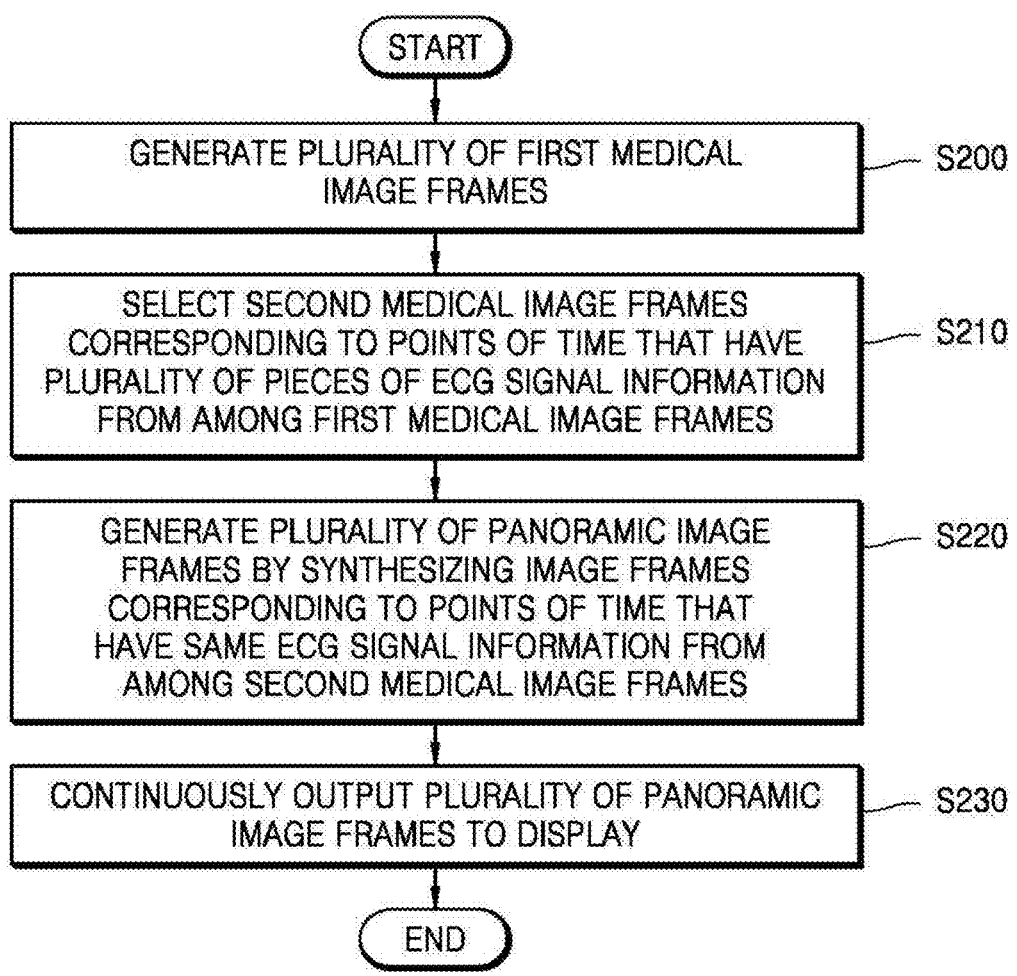
FIG. 4 is a flowchart of a method of synthesizing medical images to generate a plurality of panoramic images, according to an exemplary embodiment.

FIG. 4 is a flowchart of a method of synthesizing medical images to generate a plurality of panoramic images, according to an exemplary embodiment.

Operation S200 corresponds to operation S100 of FIG. 3, and thus, a detailed explanation thereof will not be given.

In operation S210, the apparatus 100 selects second medical image frames corresponding to points of time that have a plurality of pieces of ECG signal information of an object from among the first medical image frames that are generated in operation S200.

In operation S220, the apparatus 1000 generates a plurality of panoramic image frames by synthesizing image frames corresponding to points of time that have the same ECG signal information among the second medical image frames that are selected in operation S210, which will be explained below in detail with reference to FIG. 10.

In operation S230, the apparatus 1000 continuously outputs the plurality of panoramic image frames that are generated in operation S220 to the display 1400, which will be explained below in detail with reference to FIGS. 11 through 14.

Figure 5:
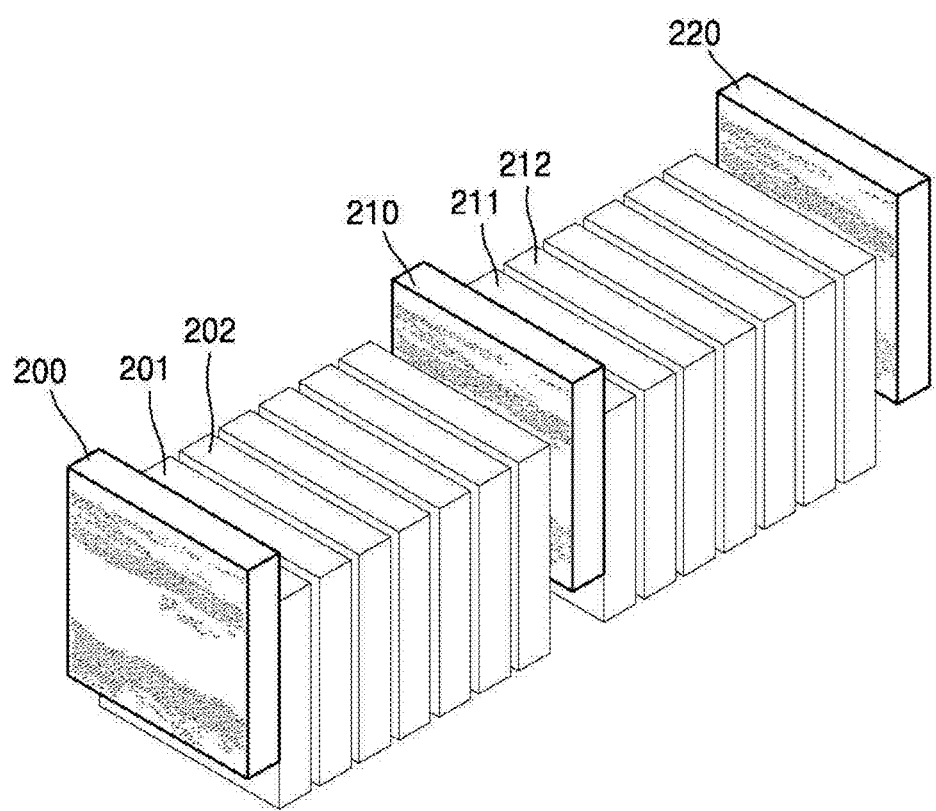
FIG. 5 is a perspective view of first medical image frames that are continuously obtained by an ultrasound diagnostic apparatus, according to an exemplary embodiment.

FIG. 5 is a perspective view illustrating first medical image frames that are continuously obtained by the apparatus 1000, according to an exemplary embodiment.

In an exemplary embodiment, the apparatus 1000 may acquire ultrasound image data by continuously transmitting ultrasound signals to the object 10 while moving the probe 20 along a surface of the object 10 and continuously receiving echo signals reflected from the object 10. In this case, the apparatus 1000 may generate a plurality of first medical image frames, as shown in FIG. 5, based on the continuously acquired ultrasound image data.

For example, the plurality of first medical image frames that are a plurality of medical image frames including image frames 200, 201 202, 210, 211, 212, and 220 may be image frames that are continuously acquired while the probe 20 moves along a surface of the object 10 for a predetermined period of time and may reflect a body movement related to a physical activity of the object 10 which occurs during a medical procedure.

Examples of the body movement related to the physical activity of the object may include, but are not limited to, a change in a thickness of a blood vessel and a change in a muscle type according to a heartbeat of the object 10.

Also, examples of the body movement related to the physical activity of the object 10 according to an exemplary embodiment may include a contraction or expansion of the heart of the object 10 and bio-signal information of the object 10 may include ECG signal information of the object 10.

For example, the first medical image frames may be obtained while the ECG signal information of the object is generated.

A conventional ultrasound diagnostic apparatus generates panoramic images by sequentially synthesizing a plurality of medical image frames that are continuously obtained in real time as shown in FIG. 5.

In general, panoramic imaging, which is a process of generating an image with a field of view greater than a field of view of an independent frame that is generated from one transducer, increases a field of view of an image to be equal to or greater than a field of view of a transducer that is generally limited.

For example, in panoramic imaging, a scan plane may be extended by manually moving a transducer in a direction parallel to the scan plane. At the same time, old echo signal information of previous frames may be retained while a new echo signal is added in order to generate an image in a direction in which the scan plane moves. A greater field of view obtained as a result may show a large organ or a wide anatomical region on one image. While the new echo signal that is obtained while the transducer moves is added, it may be very important to accurately locate the new echo signal on an existing image. This is accomplished by correlating locations of echo signals common to adjacent frames so that new information on a new frame is located accurately.

However, since ultrasound image frames that are continuously obtained during a medical procedure reflect the physical activity of the object 10, for example, the change in the blood vessel or the change in the muscle type according to the heartbeat of the object 10 as described above, connectivity between regions of interest in panoramic images that are generated by sequentially synthesizing the continuously obtained ultrasound image frames is reduced.

Also, since panoramic images show wide regions of interest but do not provide a video function of reflecting movements in the wide regions of interest, it may be difficult to detect the movements in the wide regions of interest as time passes.

In contrast, the apparatus 1000 according to an exemplary embodiment may select only some from among a plurality of medical image frames that are continuously obtained in consideration of the bio-signal information corresponding to the physical activity of the object 10 and may synthesize a panoramic image, thereby outputting the panoramic image with high accuracy. According to an exemplary embodiment, the term "panoramic image" may refer to an image including information obtained from a wide field of view which is wider than a field of view of a single image frame. However, exemplary embodiments are not limited thereto, and the term "panoramic image" may refer to an image including information obtained from a field of view which changes according to the movement of the probe 20 along a single direction of an object, along multiple directions of the object, at a single angle, at multiple angles, 2-D images, 3-D images, etc. The term "panoramic image" is not limited to any specific type of image.

For example, the apparatus 1000 according to an exemplary embodiment may generate a panoramic image by selecting and synthesizing only medical image frames corresponding to points of time that have the same ECG signal information from among a plurality of medical image frames that are continuously obtained.

For example, when medical image frames correspond to points of time that have the same ECG signal information of the object 10, this correlation may indicate that the medical image frames correspond to points of time that have the same contractions or expansions of the heart of the object 10.

In this case, consistency of a state of observed tissue of the object 10 that is included in the medical image frames corresponding to the points of time that have the same contractions or expansions of the heart of the object 10 may be maintained. For example, consistency of the thickness of the blood vessel or the muscle type included in the medical image frames corresponding to the points of time that have the same ECG signal information of the object 10 may be maintained.

Accordingly, a panoramic image in which connectivity between regions of interest is improved may be generated by synthesizing only the medical image frames corresponding to the points of time that have the same ECG signal information of the object 10.

That is, the apparatus 1000 according to an exemplary embodiment may provide a panoramic image with improved connectivity between regions of interest by generating the panoramic images by synthesizing only a plurality of second medical image frames 200, 210, and 220 corresponding to points of time that have the same ECG signal information of the object 10 among the plurality of first medical image frames of FIG. 5.

Figure 6:
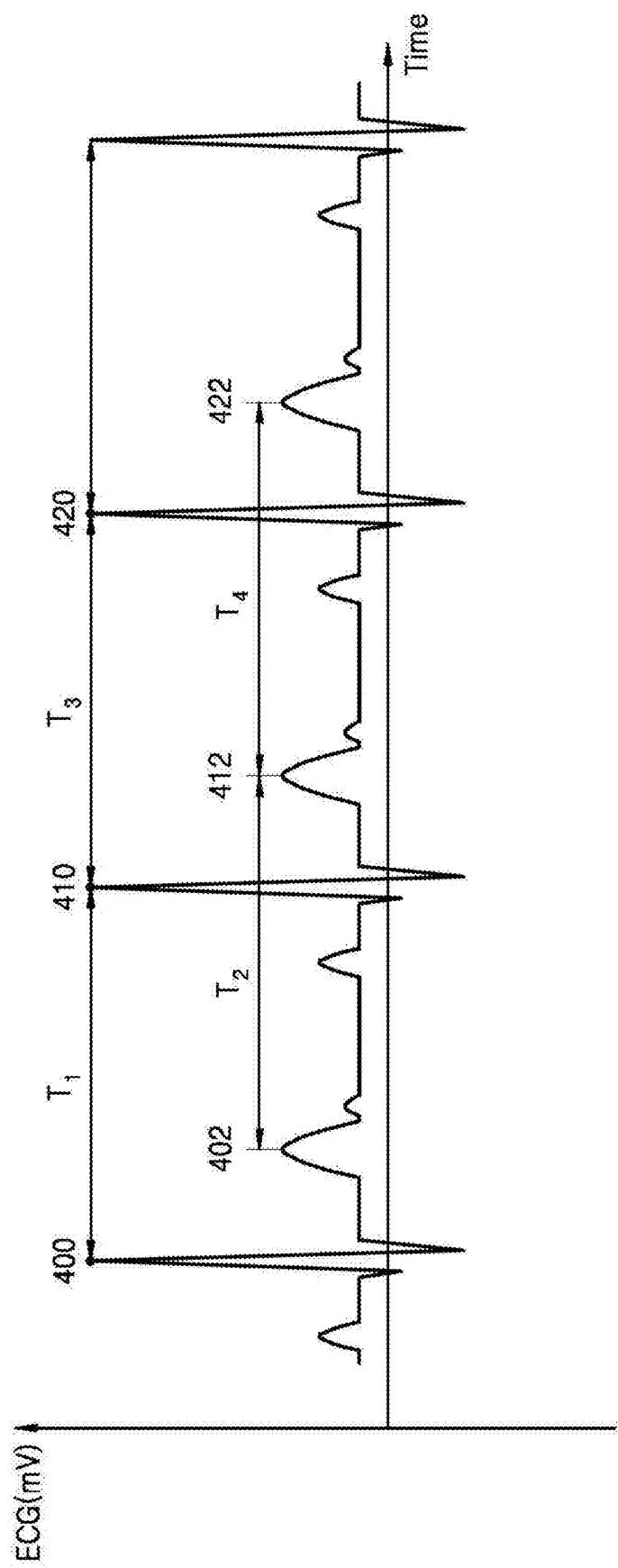
FIG. 6 is a graph illustrating electrocardiogram (ECG) signal information of an object, according to an exemplary embodiment.

FIG. 6 is a graph illustrating ECG signal information of an object, according to an exemplary embodiment. Bio-signal information according to an exemplary embodiment may indicate a body movement related to a physical activity of the object which occurs while first medical image frames are generated.

The bio-signal information according to an exemplary embodiment may be determined based on the medical image that is generated by another apparatus for obtaining medical images before the apparatus 1000 according to an exemplary embodiment performs a medical procedure. This feature is possible on the assumption that the body movement of the object is similarly maintained before and after the medical procedure is performed.

For example, the medical image that is generated by the apparatus for obtaining medical images may be a medical image obtained by previously taking a picture of a periodic body movement of the object before the apparatus 1000 according to an exemplary embodiment generates the first medical image frames.

For example, the medical image that is generated by the apparatus for obtaining medical images may include at least one of a blood vessel image, a musculoskeletal image, and an ECG image.

Also, while the apparatus 1000 according to an exemplary embodiment generates the first medical image frames that are continuously obtained while the probe 20 moves along a surface of the object for a predetermined period of time, the bio-signal information according to an exemplary embodiment may be obtained.

That is, while the apparatus 1000 according to an exemplary embodiment obtains ultrasound images of the object, the medical image including the bio-signal information of the object may be obtained by the apparatus for obtaining medical images.

For example, the body movement related to the physical activity of the object may be a contraction or expansion of the object and may include the ECG signal information of the object. FIG. 6 is a graph illustrating an ECG image that is a medical image including the body movement related to a heartbeat of the object.

As shown in FIG. 6, the ECG image shows an ECG that is measured from an ECG signal that is received through a plurality of electrodes that are attached to the object.

The apparatus 1000 according to an exemplary embodiment may obtain the bio-signal information of the object based on the ECG image of FIG. 6.

In this case, the bio-signal information according to an exemplary embodiment may be time information corresponding to a cycle of the body movement of the object. For example, the bio-signal information may include information about a cycle of the heartbeat of the object that may be calculated in the ECG image.

Also, the bio-signal information according to an exemplary embodiment may include the ECG signal information of the object.

Referring to FIG. 6, the controller 1700 may extract points of time that have the same ECG signal information from the received ECG signal.

In an exemplary embodiment, the controller 1700 may calculate at least one type of information such as a length of the ECG signal in each interval, a point of time when a voltage is the highest, or a gradient of a waveform of the ECG signal from the medical image and may extract points of time that have the same (or substantially similar) ECG signal information from the ECG image. For example, the points of time that have the same ECG signal according to an exemplary embodiment may include points of time that have the same singular points extracted from the ECG image.

For example, the controller 1700 according to an exemplary embodiment may extract an R-point 400 where a voltage of a QRS group is the highest and an R-point 410 where a voltage of a QRS group of a next heartbeat is the highest in FIG. 6 as singular points.

Also, the controller 1700 according to another exemplary embodiment may extract a point 402 where a T-wave starts and a point 412 where a T-wave of the next heartbeat starts as singular points.

Also, referring to FIG. 6, the controller 1700 may extract at least one singular point for calculating a cardiac cycle from the received ECG signal.

However, the present exemplary embodiment is not limited thereto, and various points or intervals for calculating the cardiac cycle may be extracted as singular points. The controller 1700 according to an exemplary embodiment may calculate the cardiac cycle based on the extracted singular points. For example, when the R-point 400 and the R-point 410 are extracted as singular points, the controller 1700 may measure a time $T_1$ corresponding to an RR interval between the R-point 400 and the R-point 410 and may calculate the cardiac cycle based on the measured time $T_1$. For example, when the time $T_1$ corresponding to the RR interval is 0.6 seconds, the cardiac cycle may be calculated to be 0.6 seconds.

Also, when the point 402 where the T-wave starts and the point 412 where the T-wave of the next heartbeat starts are extracted as singular points, instead of extracting the R-points 400 and 410 or the RR interval as singular points, the controller 1700 may measure a time $T_2$ corresponding to a TT interval between the point 402 where the T-wave starts and the point 412 where the T-wave of the next heartbeat starts and may calculate the cardiac cycle based on the measured time $T_2$.

Figure 7:
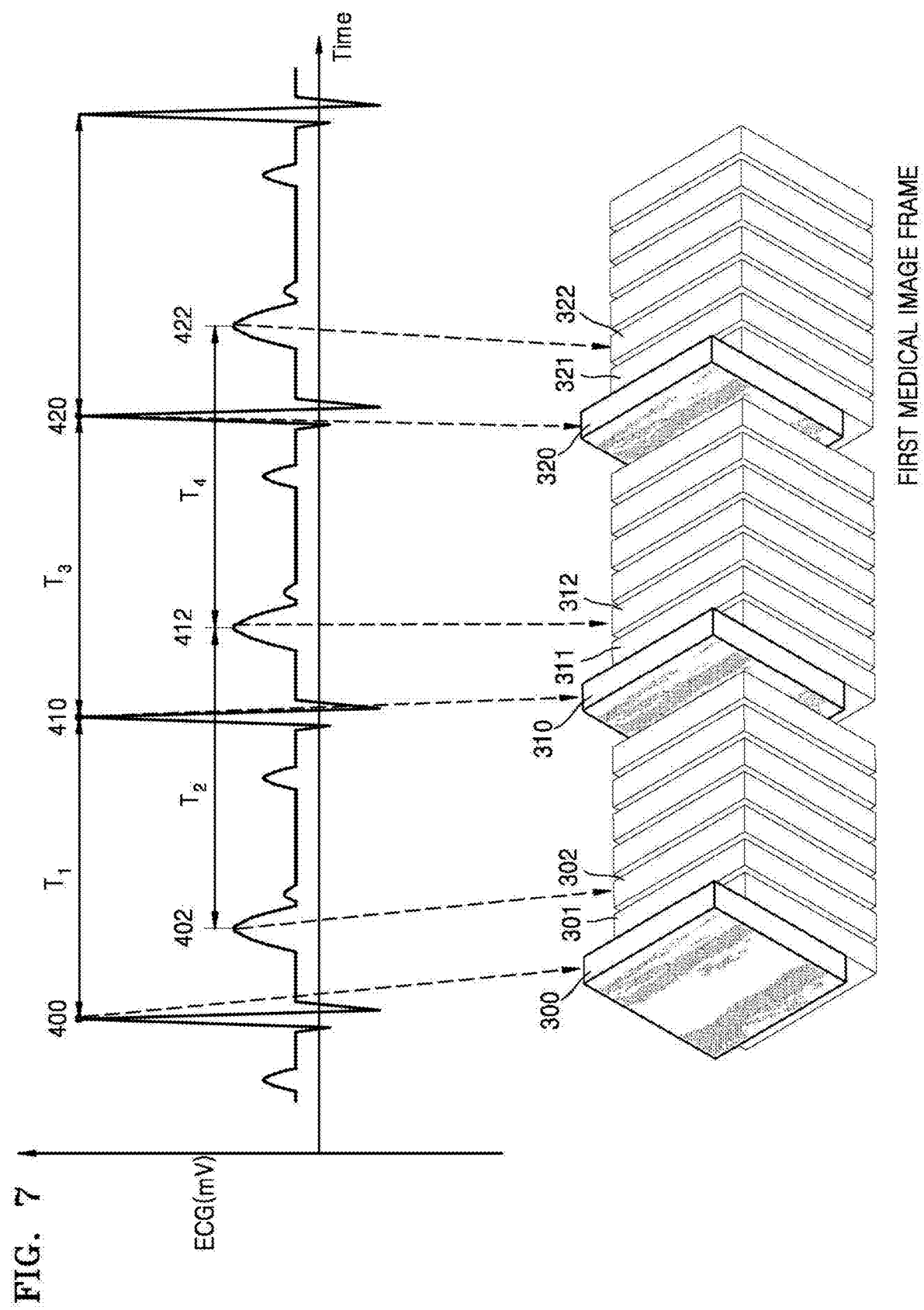
FIG. 7 shows a graph and a perspective view illustrating a correlation between ECG signal information of an object and first medical image frames, according to an exemplary embodiment.

FIG. 7 shows a graph and a perspective view illustrating a correlation between ECG signal information of an object and first medical image frames, according to an exemplary embodiment.

Since a plurality of first medical image frames according to an exemplary embodiment are image frames that are continuously obtained while the probe 20 moves along a surface of the object for a predetermined period of time and a physical activity of the object continuously occurs during the predetermined period of time, information related to a periodic body movement of the object may be included in the first medical image frames.

However, since image processing of generating a panoramic image performed by the apparatus 1000 according to an exemplary embodiment is a part of a pre-process that is performed before data is stored in a memory, it may be difficult to detect the periodic body movement of the object by analyzing the plurality of first medical image frames.

Accordingly, on the assumption that consistency of the periodic body movement of the object is maintained before or after an ultrasound medical procedure, bio-signal information according to an exemplary embodiment may be obtained from at least one medical image that is previously generated by an apparatus for obtaining medical images, instead of from the first medical image frames according to an exemplary embodiment. For example, the at least one medical image that reflects the periodic body movement of the object may include at least one of a blood vessel image, a musculosketal image, and an ECG image.

The apparatus 1000 according to an exemplary embodiment may correlate the bio-signal information that is obtained based on the at least one medical image that is previously generated before ultrasound imaging with the first medical image frames that are generated in real time during the ultrasound imaging.

For example, although a time when the apparatus 1000 according to an exemplary embodiment generates the first medical image frames and a time when the apparatus for obtaining medical images according to an exemplary embodiment generates the at least one medical image for extracting the bio-signal information are different from each other, since consistency of the periodic body movement of the object is maintained irrespective of a time when imaging is performed, as shown in FIG. 7, the at least one medical image and the first medical image frames may be correlated with each other in relation to the periodic body movement that is the physical activity of the object. Accordingly, the periodic body movement of the object that is included in the first medical image frames may be derived from the periodic body movement of the object that is calculated from the at least one medical image.

As shown in FIG. 6, when the body movement of the object that is included in the at least one medical image is periodic and, in this case, time information corresponding to a cycle of the body movement of the object is T (sec), the apparatus 1000 according to an exemplary embodiment may synthesize panoramic images by obtaining the plurality of first medical image frames using an imaging time of at least 2 T (sec) as shown in FIG. 7.

As shown in FIG. 7, it may be derived that a movement of the object at the R-points 400, 410, and 420 where a voltage is the highest in each cycle of the medical image that is the ECG image of FIG. 6 respectively correspond to a movement of the object in the medical image frames 300, 310, and 320 in the first medical image frames of FIG. 5.

For example, in relation to the physical activity of the heartbeat of the object, a change in a thickness of a blood vessel of the object periodically occurs according to periodic contractions or expansions of the heart corresponding to a pumping action of the heart that supplies blood to all body parts.

As shown in FIG. 7, the time $T_1$ that is a cardiac cycle calculated based on the R-point 400 and the R-point 410 that are extracted as singular points in the ECG image may be obtained as the bio-signal information including time information corresponding to a cycle of the body movement of the object.

In this case, a body movement corresponding to the R-points 400, 410, and 420 where the voltage of the QRS group in the ECG image is the highest may be a contraction of the heart, and thus, blood is supplied to all body parts, thereby causing a thickness of a blood vessel included in the first medical image frames to become greater than usual.

That is, the thickness of the blood vessel included in the first medical image frames according to an exemplary embodiment may vary according to the cardiac cycle of the object in the ECG image according to an exemplary embodiment. Also, the change in the thickness of the blood vessel that occurs according to the pumping action of the heart is periodic, like the cardiac cycle. A cycle of a change in the thickness of the blood vessel including the first medical image frames may be derived by using the time $T_1$ that the cardiac cycle already obtained in the ECG image.

For example, when the second medical image frame 300 corresponding to the R-point 400 where the voltage of the QRS group in the ECG image is the highest is determined, the second medical image frames 310 and 320 in other cycles may also be determined based on the time $T_1$ that is the cardiac cycle. Accordingly, the apparatus 1000 according to an exemplary embodiment may select the plurality of second medical image frames 300, 310, and 320 respectively corresponding to the plurality of R-points 400, 410, and 420 in different cycles by using the bio-signal information that is obtained in the ECG image.

In contrast, when a body movement corresponding to points 402, 412, and 422 where the T-wave starts in the ECG image is an expansion of the heart, the thickness of the blood vessel included in the first medical image frames may get less than usual. For example, when the second medical image frame 302 corresponding to the point 402 where the T-wave starts in the ECG image is determined, the second medical image frames 312 and 322 in other cycles may also be determined based on the time $T_2$ that is a cardiac cycle.

As described above, a periodic body movement of the object that is included in the first medical image frames that are continuously obtained by the apparatus 1000 according to an exemplary embodiment may be derived from the bio-signal information that is obtained in the at least one medical image. In this case, the bio-signal information may include at least one of time information corresponding to a cycle of the body movement of the object, for example, a cardiac cycle, and state information corresponding to the body movement of the object, for example, a state of a thickness of a blood vessel.

In this case, since the apparatus 1000 according to an exemplary embodiment generates panoramic images by synthesizing only second medical image frames that are derived to have the same body movement among the plurality of first medical image frames, the apparatus 1000 may generate the panoramic images in consideration of the physical activity of the object, which will be explained below with reference to FIGS. 8 through 10.

While the apparatus 1000 according to an exemplary embodiment obtains the first medical image frames of the object as shown in FIG. 7, the ECG image including the ECG signal information of the object may be obtained by the apparatus for obtaining medical images.

In this case, as shown in FIG. 7, the ECG signal information of the ECG image and the first medical image frames may be correlated with each other.

For example, the ECG signal information of the ECG image may be calculated based on at least one type of information such as a length of the ECG signal in each interval, a point of time when a voltage is the highest, and a gradient of a waveform.

Also, the apparatus 1000 according to an exemplary embodiment may extract points of time that have the same ECG signal information from the ECG image as shown in FIG. 7.

For example, the points of time that have the same ECG signal information according to an exemplary embodiment may include points of time that have the same singular points extracted in the ECG image.

As shown in FIG. 7, the R-points 400, 410, and 420 where the voltage of the QRS group in the ECG image is the highest may correspond to the points of time that are the same ECG signal information. In this case, the second medical image frames 300, 310, and 320 respectively corresponding to the R-points 400, 410, and 420 in the ECG image may be selected from among the first medical image frames.

Alternatively, the points 402, 412, and 422 where the T-wave starts in the ECG image may correspond to the points of time that have the same ECG signal information. In this case, the second medical image frames 302, 312, and 322 respectively corresponding to the points 402, 412, and 422 where the T-wave starts in the ECG image may be selected from among the first medical image frames.

Figure 8:
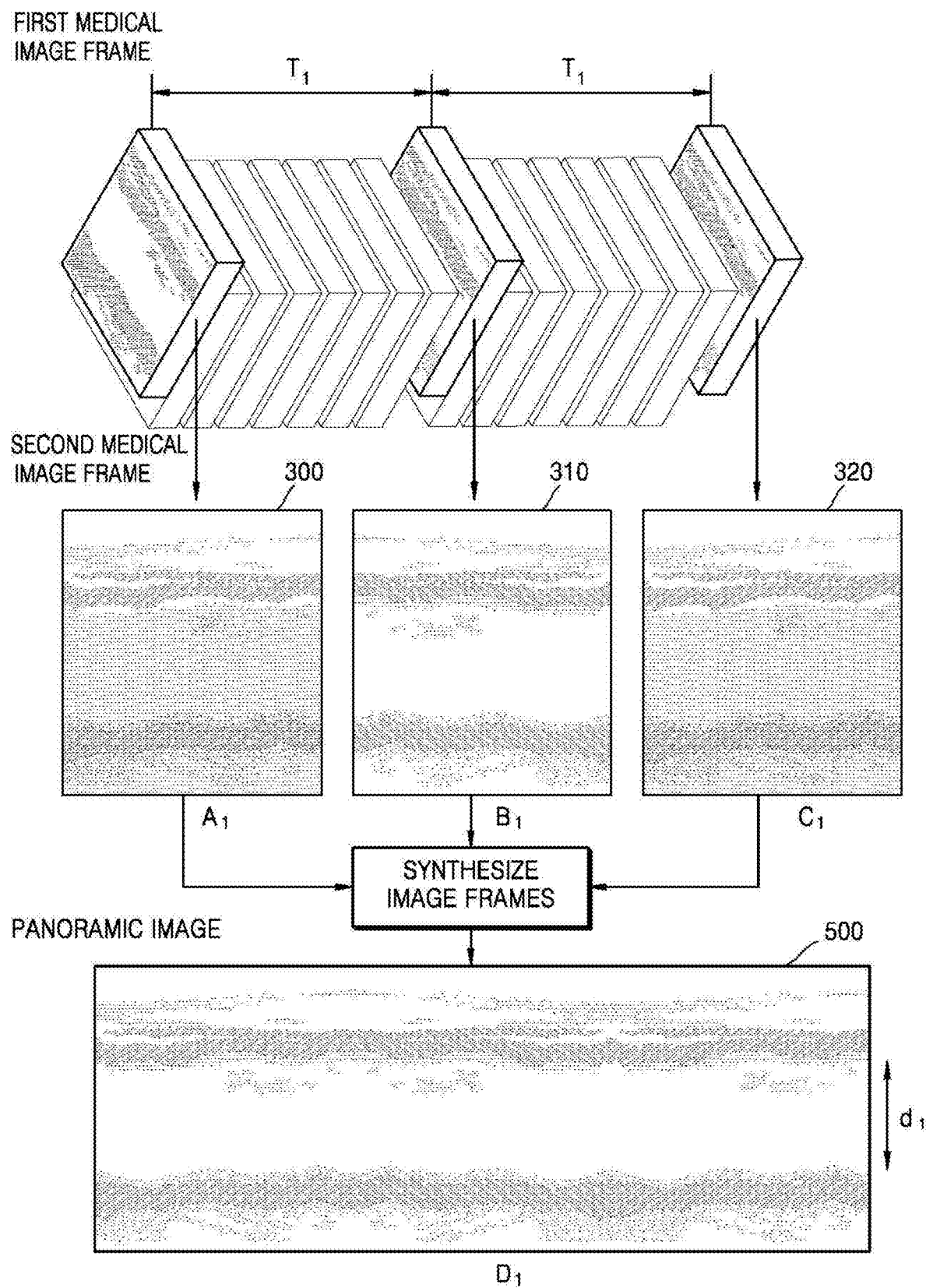
FIGS. 8 and 9 are views illustrating various examples where the ultrasound diagnostic apparatus generates panoramic images by selecting and synthesizing second medical image frames corresponding to points of time that have the same ECG signal information of an object among first medical image frames, according to an exemplary embodiment.
Figure 9:
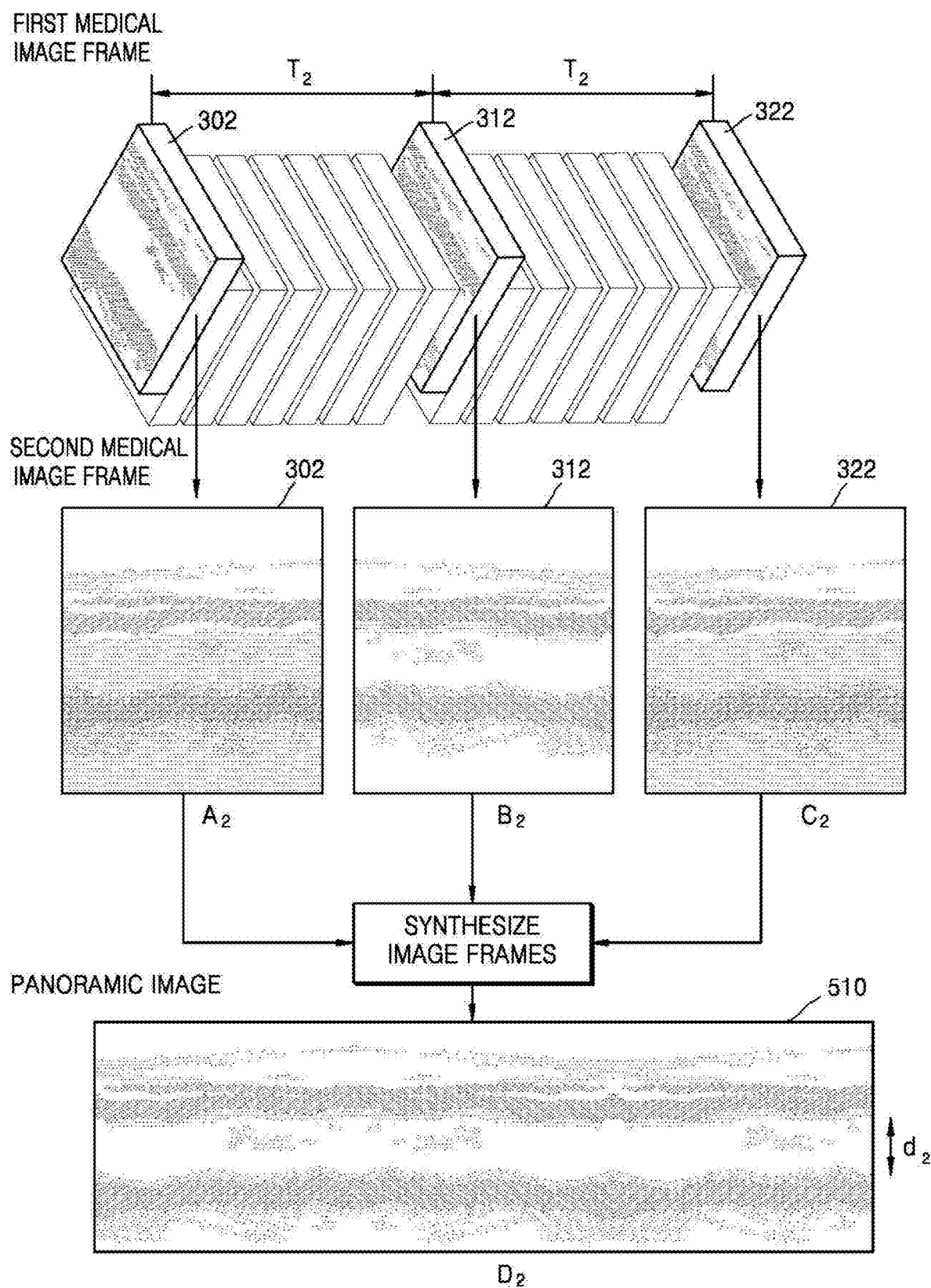

FIGS. 8 and 9 are views illustrating various examples where the apparatus 1000 generates panoramic images by synthesizing second medical image frames corresponding to points of time that have the same ECG signal information among first medical image frames, according to an exemplary embodiment.

As shown in FIG. 7, the second medical image frames 300, 310, and 320 respectively corresponding to the R-points 400, 410, and 420 in the ECG image may be selected from among the first medical image frames. In this case, a body movement of an object included in the second medical image frames 300, 310, and 320 includes a state where a blood vessel is relatively expanded to be wide.

The apparatus 1000 according to an exemplary embodiment may generate a panoramic image $D_1$ 500 by selecting and synthesizing only second medical image frames $A_1$, $B_1$, and $C_1$ that correspond to points of time that have the same ECG signal information of the object and thus are derived to have the same thickness of a blood vessel in the first medical image frames. In this case, as shown in FIG. 8, since the panoramic image $D_1$ 500 is obtained by selecting and synthesizing only image frames corresponding to a state where the blood vessel is expanded (e.g., a thickness of the blood vessel is $d_1$) in a periodic body movement of the object and only the panoramic image $D_1$ 500 in the state where the blood vessel is expanded is displayed, connectivity between regions of interest may be improved. For example, the apparatus 1000 may synthesize the second medical image frames $A_1$, $B_1$, and $C_1$ by using a synthesis algorithm which combines the second medical image frames $A_1$, $B_1$, and $C_1$ side-by-side or in some other continuous form, although is not limited thereto.

Also, as shown in FIG. 7, the second medical image frames 302, 312, and 322 respectively corresponding to the points 402, 412, and 422 where the T-wave starts in the ECG image may be selected from among the first medical image frames. In this case, a body movement of the object included in the second medical image frames 302, 312, and 322 includes a state where the blood vessel is relatively contracted to be narrow.

The apparatus 1000 according to an exemplary embodiment may generate a panoramic image $D_2$ 510 by selecting and synthesizing only second medical image frames $A_2$, $B_2$, and $C_2$ that correspond to points of time that have the same ECG signal information of the object and thus are derived to have the same thickness of the blood vessel in the first medical image frames. In this case, as shown in FIG. 9, since the panoramic image $D_2$ 510 is obtained by selecting and synthesizing only image frames corresponding to a state where the blood vessel is contracted (e.g., a thickness of the blood vessel is $d_2$) in the periodic body movement of the object and only the panoramic image $D_2$ 510 in the state where the blood vessel is contracted is displayed, connectivity between regions of interest may be improved.

Figure 10:
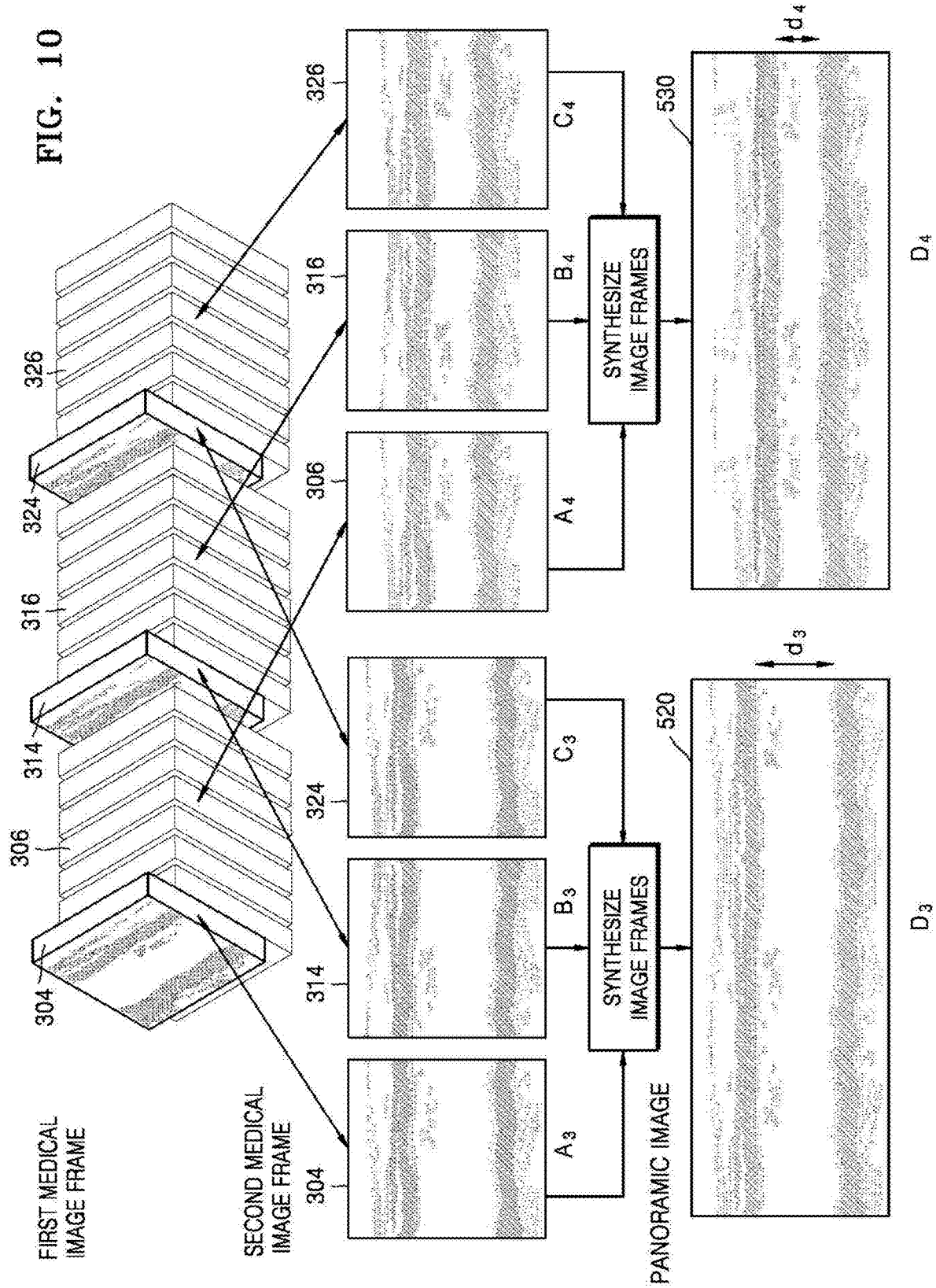
FIG. 10 is a view illustrating an example where the ultrasound diagnostic apparatus generates a plurality of panoramic images by synthesizing image frames corresponding to points of time that have the same ECG signal information of an object among first medical image frames, according to an exemplary embodiment.

FIG. 10 is a view illustrating an example where the apparatus 1000 generates a plurality of panoramic images by synthesizing image frames corresponding to points of time that have the same ECG signal information of an object among first medical image frames, according to an exemplary embodiment.

As shown in FIG. 10, the apparatus 1000 according to an exemplary embodiment may select a plurality of second medical image frames having a plurality of pieces of ECG signal information and may generate a plurality of panoramic images. In this case, the panoramic images according to an exemplary embodiment may be generated by synthesizing second medical image frames corresponding to points of time that have the same ECG signal information.

As shown in FIG. 10, second medical image frames 304, 314, and 324 respectively corresponding to the R-points 400, 410, and 420 in the ECG image and second medical image frames 306, 316, and 326 respectively corresponding to the points 402, 412, and 422 where the T-wave starts in the ECG image may be selected from among first medical image frames.

In this case, a panoramic image $D_3$ 520 may be generated by synthesizing only second medical image frames $A_3$, $B_3$, and $C_3$ having bio-signal information corresponding to a state where a blood vessel is expanded (e.g., a thickness of the blood vessel is $d_3$). Also, a panoramic image $D_4$ 530 may be generated by synthesizing only second medical image frames $A_4$, $B_4$, and $C_4$ having bio-signal information corresponding to a state where the blood vessel is contracted (e.g., a thickness of the blood vessel is $d_4$).

In this case, the apparatus 1000 according to an exemplary embodiment may generate a plurality of panoramic images by synthesizing second medical image frames corresponding to points of time that have the same ECG signal information of the object from among the same first medical image frames. Accordingly, the apparatus 1000 according to an exemplary embodiment may provide a panoramic video function by continuously outputting the plurality of panoramic images corresponding to points of various body movements of the object.

FIGS. 11 through 14 are views illustrating various examples where the apparatus 1000 displays generated panoramic images, according to an exemplary embodiment.

Figure 11:
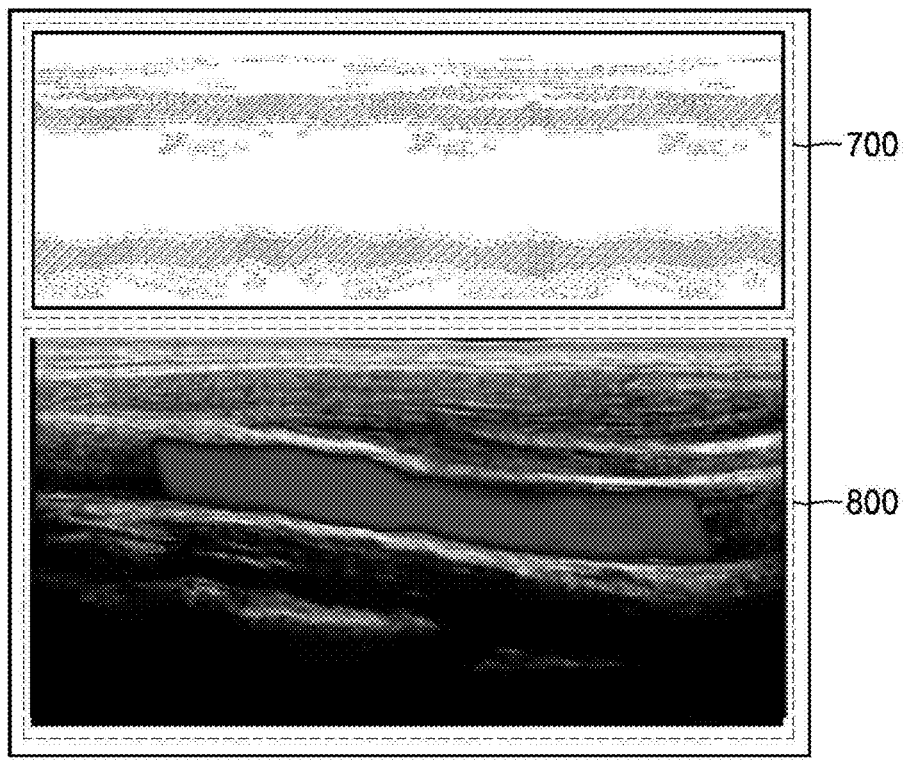
Figure 12:
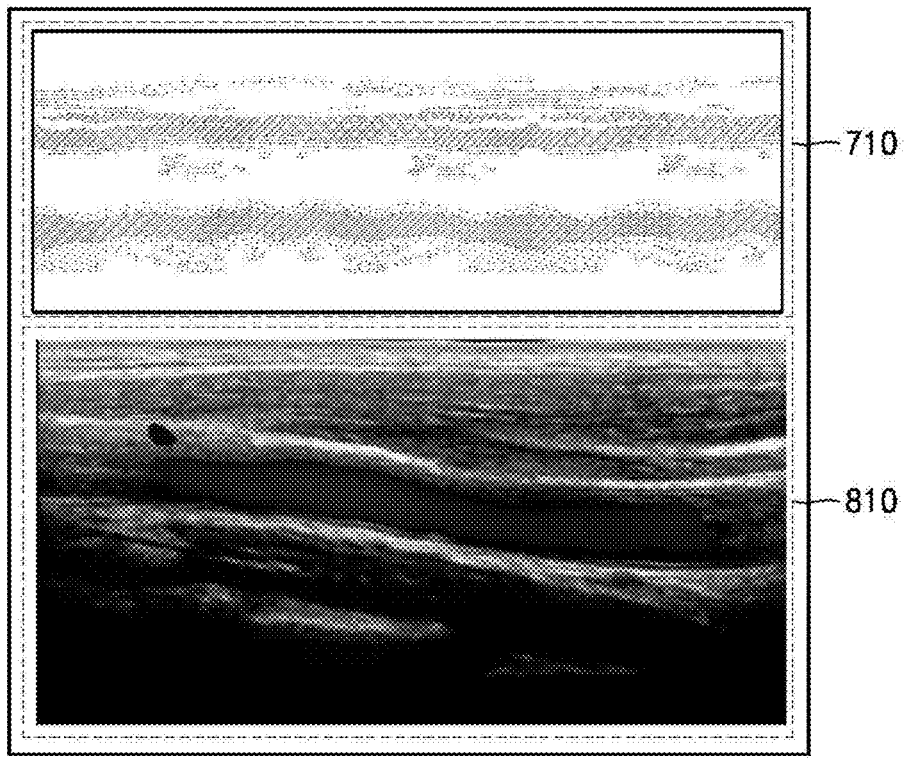

As shown in FIGS. 11 and 12, Doppler images 800 and 810 that may show a movement of blood flow in various colors and/or B-mode images 700 and 710, wherein the Doppler images 800 and 810 and the B-mode images 700 and 710 are panoramic images, may be displayed on the display 1400 of the apparatus 1000.

The B-mode image 700 and the Doppler image 800 of FIG. 11 show the panoramic image $D_3$ 520 that is generated by synthesizing only the second medical image frames $A_3$, $B_3$, and $C_3$ having a bio-signal information corresponding to a state where a blood vessel is expanded (e.g., a thickness of the blood vessel is $d_3$) in FIG. 10.

Also, the B-mode image 710 and the Doppler image 810 of FIG. 12 show the panoramic image $D_4$ 530 that is generated by synthesizing only the second medical image frames $A_4$, $B_4$, and $C_4$ having bio-signal information corresponding to a state where the blood vessel is contracted (e.g., a thickness of the blood vessel is $d_4$) in FIG. 10.

For example, images 720 and 820 of FIGS. 13A and 13B show the panoramic image $D_4$ 530 that is generated by synthesizing only second medical image frames having bio-signal information corresponding to a state where a blood vessel of a wrist is contracted.

Figure 14A:
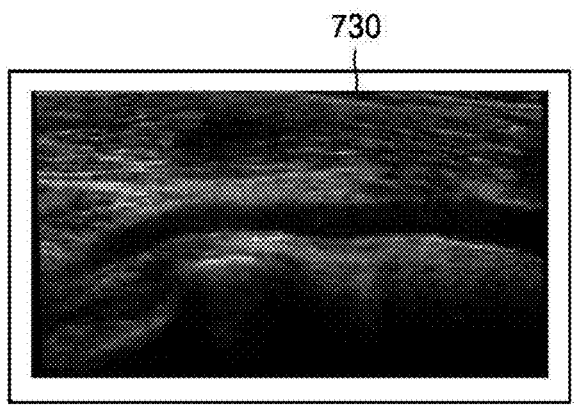
Figure 14B:
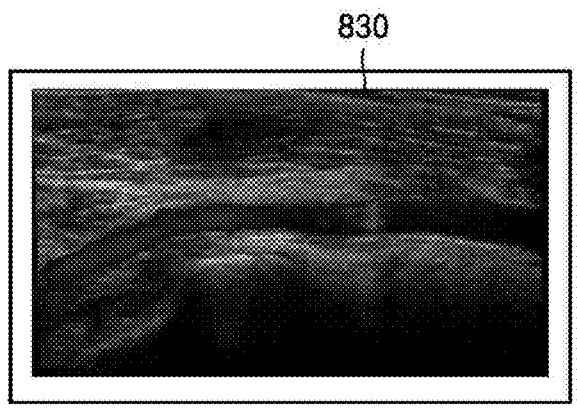

Also, images 730 and 830 of FIGS. 14A and 14B show the panoramic image $D_4$ 530 that is generated by synthesizing only second medical image frames having bio-signal information corresponding to a state where a blood vessel of a back portion of a lower leg is contracted.

Figure 15:
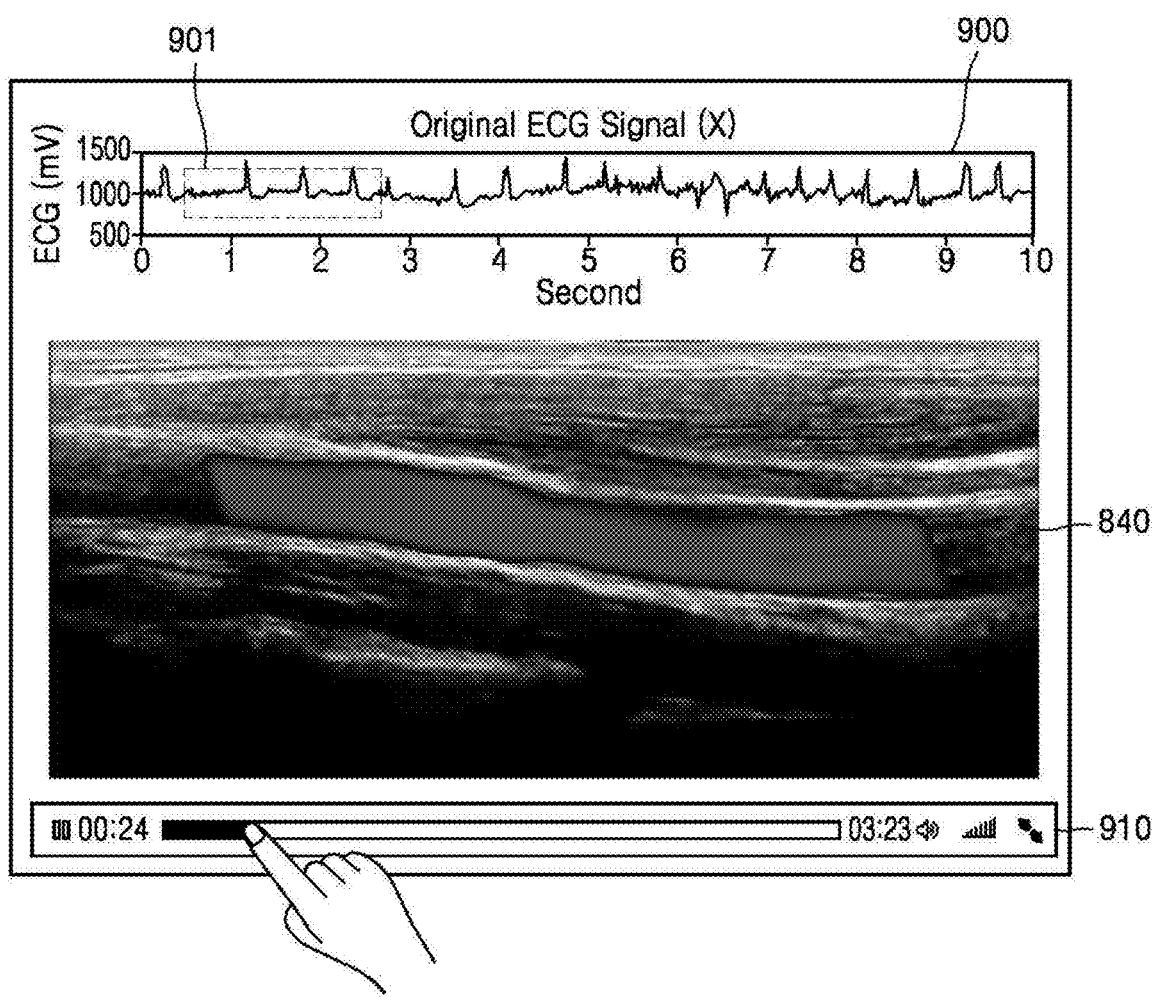
FIGS. 15, 16 and 17 are views illustrating various examples where the ultrasound diagnostic apparatus displays panoramic images along with ECG signal information of an object, according to an exemplary embodiment.
Figure 16:
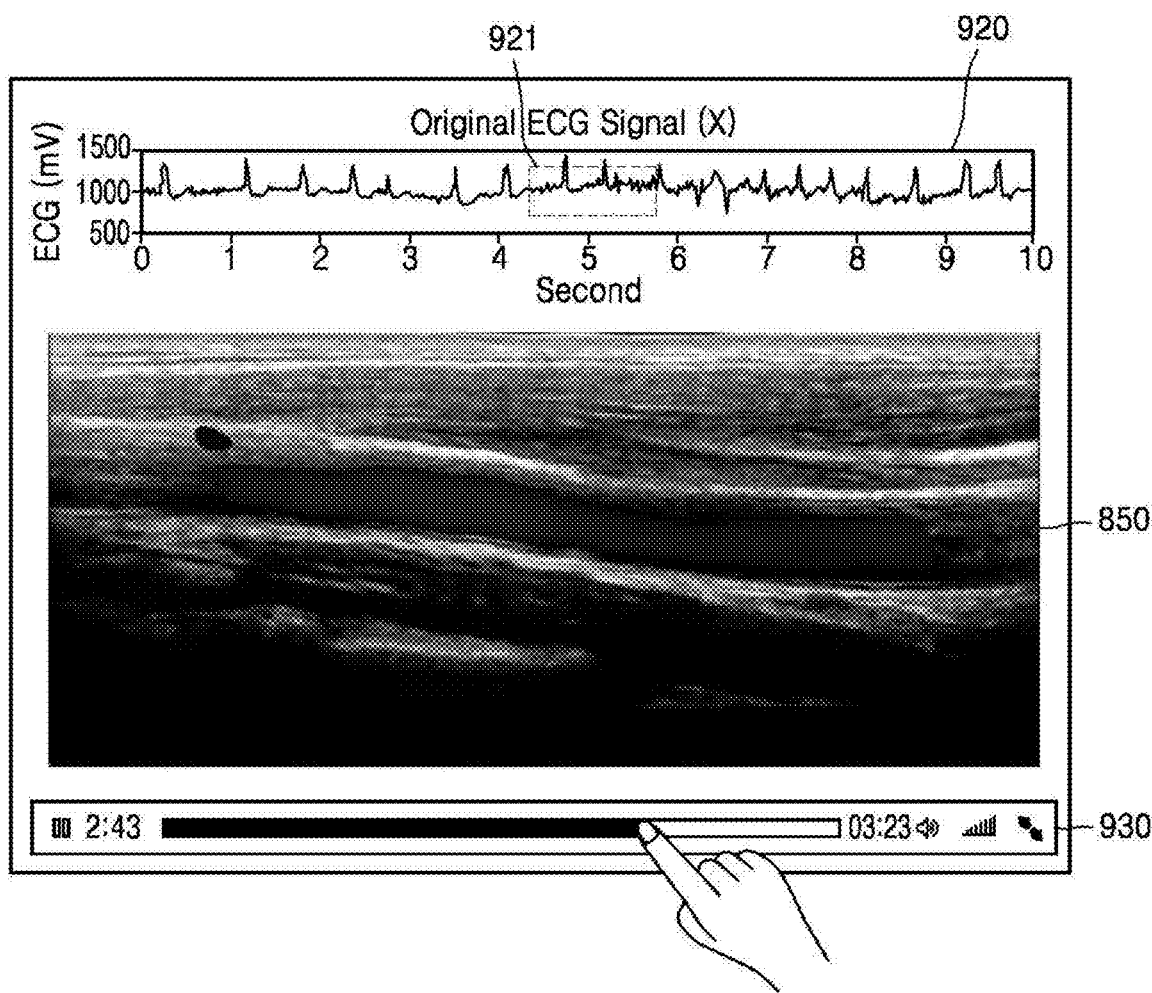
Figure 17:
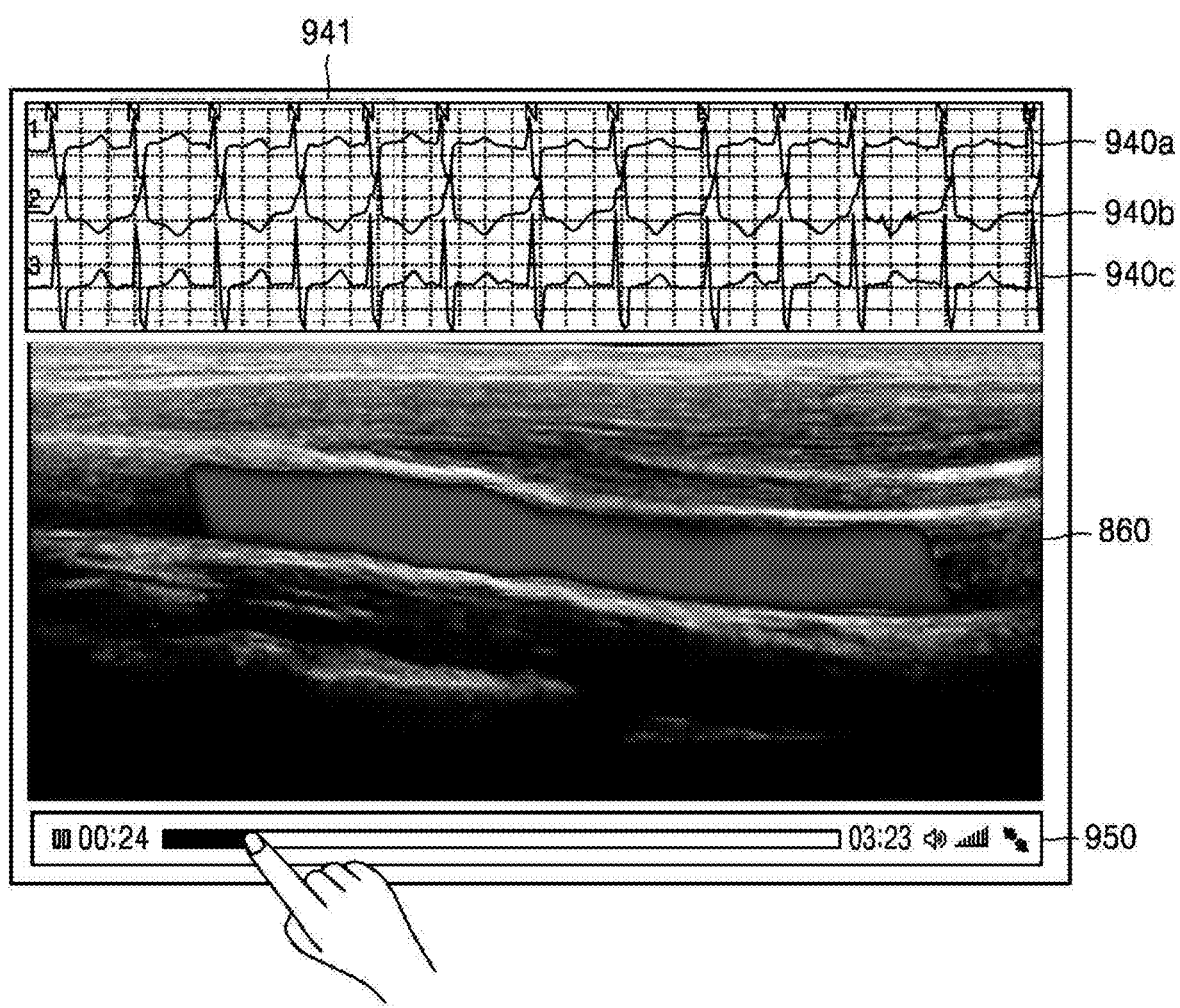

FIGS. 15 through 17 are views illustrating various examples where the apparatus 1000 displays panoramic images along with ECG signal information of an object, according to an exemplary embodiment.

FIGS. 15 through 17 are views for explaining a post-process of processing panoramic images by using ECG signal information of an object after the panoramic images are generated and stored in a memory. An image process unit according to an exemplary embodiment may correlate the ECG signal information of the object with the panoramic images and may store the ECG signal information and the panoramic images that are correlated with each other, and a display according to an exemplary embodiment may display the ECG signal information and the panoramic images together.

In this case, the plurality of panoramic images according to an exemplary embodiment may be correlated with the ECG signal information of the object and may be stored as a video file in the memory.

For example, as shown in FIG. 15, a panoramic image 840 that is generated by synthesizing only second medical image frames corresponding to points of time that have the same ECG signal information of the object may be displayed on the display along with an ECG image 900 of the object.

In this case, a GUI related to a function of reproducing a panoramic video may also be output to the display.

For example, the GUI related to the function of reproducing the panoramic video may include a user interface for reproducing, editing, or re-storing the panoramic images.

For example, as shown in FIG. 15, when the panoramic image 840 that is stored in the memory is output, the display may display together the ECG image 900 correlated with the panoramic image 840, an interval marker 901 of the ECG image 900 corresponding to the panoramic image 840 that is currently output to the display, and a processor bar 910.

Also, as shown in FIG. 16, when a panoramic image 850 that is stored in the memory is output, the display may display together an ECG image 920 correlated with the panoramic image 850, an interval marker 921 of the ECG image 920 corresponding to the panoramic image 850 that is currently output to the display, and a processor bar 930.

Also, as shown in FIG. 17, the display may also output a plurality of ECG images 940a, 940b, and 940c that are correlated with a panoramic image 860.

Also, the apparatus 1000 according to an exemplary embodiment may reproduce, edit, or re-store an interval of a panoramic image selected by a user through a user interface related to a function of reproducing the panoramic image.

For example, as shown in FIGS. 15 through 17, only an interval of a panoramic image desired to be seen by the user may be output to the display based on a user input through the processor bars 910, 930, and 950.

Also, the apparatus 1000 according to an exemplary embodiment may store in the memory, as a separate file, only a panoramic image that is selected based on a user input in a panoramic video file that is stored in the memory. In this case, the selected panoramic image may be correlated with ECG signal information corresponding to the selected panoramic image and may be stored in the memory.

For example, when the user selects an interval that is determined to have an abnormality in the ECG image output to the display, a panoramic image corresponding to the interval may be output. Also, only the panoramic image corresponding to the interval that is determined to have an abnormality in an ECG signal may be re-stored in the memory based on the user's input.

Accordingly, since the apparatus 1000 according to an exemplary embodiment provides panoramic images in consideration of a periodic body movement of the object, and thus, may obtain more physical information than that obtained by using panoramic images that are provided as still images, the apparatus 100 may be used for various medical tests.

For example, the apparatus 1000 according to an exemplary embodiment may detect a contraction or expansion of a blood vessel or a position and the amount of a blood clot by using a panoramic video function. Also, the apparatus 1000 according to an exemplary embodiment may be used to evaluate blood flow in an artery or examine an aortic aneurysm, and may use a panoramic video function to evaluate a state where a blood vessel is reconnected after blood vessel bypass surgery.

Also, since the apparatus 1000 according to an exemplary embodiment provides a function of reproducing, editing, or re-storing a panoramic image of an interval desired by the user through a user interface related to a function of reproducing the panoramic video, the apparatus 1000 may provide to the user a panoramic video function having high intuition and high utilization.

While one or more exemplary embodiments have been described with reference to the figures, it will be understood by one of ordinary skill in the art that various changes in form and details may be made therein without departing from the spirit and scope of the exemplary embodiments as defined by the following claims.

What is claimed is:

1. A method of synthesizing medical images, the method comprising:
acquiring image data of an object;
generating first medical image frames of the object, based on the acquired image data;
displaying, on a display, electrocardiogram (ECG) signal information corresponding to the generated first medical image frames;
storing a first video file including a panoramic video including a first panoramic image and a second panoramic image;
receiving a first user input of selecting a time point of the panoramic video;
in response to the first user input being received, displaying an interval marker, identifying a time interval of the displayed ECG signal information corresponding to the selected time point of the panoramic video, on the displayed ECG signal information, while displaying a portion of the panoramic video corresponding to the selected time point;
receiving a second user input of selecting the portion of the panoramic video to be stored; and
in response to the second user input being received, storing a second video file including a subset of the panoramic video corresponding to the portion of the panoramic video,
wherein the first panoramic image is generated by synthesizing second medical image frames corresponding to R-points of time at which voltages of the ECG signal information are highest in the selected time interval, among the generated first medical image frames, and
the second panoramic image is generated by synthesizing third medical image frames corresponding to T-points of time at which T-waves of the ECG signal information start in the selected time interval, among the generated first medical image frames.

2. The method of claim 1, wherein the acquiring of the image data of the object comprises:
transmitting an ultrasound signal to the object;
receiving a response signal, based on the ultrasound signal that is transmitted; and
acquiring the image data, based on the response signal that is received.

3. The method of claim 1, wherein the acquiring of the image data of the object comprises
transmitting a radio frequency (RF) signal to the object;
receiving a magnetic resonance (MR) signal that is emitted from the object, based on the RF signal that is transmitted; and
acquiring the image data, based on the MR signal that is received.

4. The method of claim 1, wherein the acquiring of the image data of the object comprises:
transmitting an X-ray signal to the object;
detecting the X-ray signal that is transmitted through the object; and
acquiring computed tomography (CT) image data, based on the X-ray signal that is detected.

5. The method of claim 1, further comprising storing, in the second video file, a portion of the ECG signal information corresponding to the portion of the panoramic video that is selected by the second user input.

6. The method of claim 1, wherein the R-points of time are singular points of time that are extracted from an ECG image.

7. An apparatus configured to synthesize medical images, the apparatus comprising:
an image processor configured to generate first medical image frames of an object, based on image data of the object;
a display configured to display electrocardiogram (ECG) signal information corresponding to the first medical image frames; and
a memory configured to store a first video file and a second video file,
wherein the image processor is further configured to:
store, in the memory, the first video file including a panoramic video including a first panoramic image and a second panoramic image;
receive a first user input of selecting a time point of the panoramic video;
in response to the first user input being received, control the display to display an interval marker, identifying a time interval of the displayed ECG signal information corresponding to the selected time point of the panoramic video, on the displayed ECG signal information, while displaying a portion of the panoramic video corresponding to the selected time point;
receive a second user input of selecting the portion of the panoramic video to be stored; and
in response to the second user input being received, store, in the memory, the second video file including a subset of the panoramic video corresponding to the portion of the panoramic video,
the first panoramic image is generated by synthesizing second medical image frames corresponding to R-points of time at which voltages of the ECG signal information are highest in the selected time interval, among the generated first medical image frames, and the second panoramic image is generated by synthesizing third medical image frames corresponding to T-points of time at which T-waves of the ECG signal information start in the selected time interval, among the generated first medical image frames.

8. The apparatus of claim 7, further comprising an ultrasound transceiver configured to:
transmit an ultrasound signal to the object;
receive a response signal, based on the ultrasound signal that is transmitted; and
acquire the image data, based on the response signal that is received.

9. The apparatus of claim 7, further comprising a radio frequency (RF) emitter configured to:
transmit a radio frequency (RF) signal to the object;
receive a magnetic resonance (MR) signal that is emitted from the object, based on the RF signal that is transmitted; and
acquire the image data, based on the MR signal that is received.

10. The apparatus of claim 7, further comprising an X-ray emitter configured to:
transmit an X-ray signal to the object;
detect the X-ray signal that is transmitted through the object; and
acquire computed tomography (CT) image data, based on the X-ray signal that is detected.

11. The apparatus of claim 7, wherein the image processor is further configured to store, in the second video file, a portion of the ECG signal information corresponding to the portion of the panoramic video that is selected by the second user input.

12. The apparatus of claim 7, wherein the R-points of time are singular points of time that are extracted from an ECG image.

13. A non-transitory computer-readable storage medium storing instructions that cause a processor to:
acquire image data of an object;
generate first medical image frames of the object, based on the acquired image data;
display, on a display, electrocardiogram (ECG) signal information corresponding to the generated first medical image frames;
store a first video file including a panoramic video including a first panoramic image and a second panoramic image;
receive a first user input of selecting a time point of the panoramic video; and
in response to the first user input being received, display an interval marker, identifying a time interval of the displayed ECG signal information corresponding to the selected time point of the panoramic video, on the displayed ECG signal information, while displaying a portion of the panoramic video corresponding to the selected time point;
receive a second user input of selecting the portion of the panoramic video to be stored; and
in response to the second user input being received, store a second video file including a subset of the panoramic video corresponding to the portion of the panoramic video,
wherein the first panoramic image is generated by synthesizing second medical image frames corresponding to R-points of time at which voltages of the ECG signal information are highest in the selected time interval, among the first medical image frames, and the second panoramic image is generated by synthesizing third medical image frames corresponding to T-points of time at which T-waves of the ECG signal information start in the selected time interval, among the generated first medical image frames.

14. An apparatus configured to generate an image, the apparatus comprising:
a probe configured to:
   transmit a signal to an object; and
   receive a response signal, based on the signal that is transmitted;
an image processor configured to generate sequential image frames, based on the received response signal;
a display configured to display electrocardiogram (ECG) signal information corresponding to the generated sequential image frames; and
a memory configured to store a first video file and a second video file;
wherein the image processor is further configured to:
   store, in the memory, the first video file including a panoramic video including a first panoramic image and a second panoramic image;
   receive a first user input of selecting a time point of the panoramic video;
   in response to the first user input being received, control the display to display an interval marker, identifying a time interval of the displayed ECG signal information corresponding to the selected time point of the panoramic video, on the displayed ECG signal information, while displaying a portion of the panoramic video corresponding to the selected time point;
   receive a second user input of selecting the portion of the panoramic video to be stored; and
   in response to the second user input being received, store, in the memory, the second video file including a subset of the panoramic video corresponding to the portion of the panoramic video,
the first panoramic image is generated by synthesizing first medical image frames corresponding to R-points of time at which voltages of the ECG signal information are highest in the selected time interval, among the generated sequential image frames, and
the second panoramic image is generated by synthesizing second medical image frames corresponding to T-points of time at which T-waves of the ECG signal information start in the selected time interval, among the generated sequential image frames.

15. The apparatus of claim 14, wherein the probe is further configured to:
   transmit the signal to the object as the probe moves along a direction of the object; and
   receive the response signal at different positions along the direction of the object, and
the panoramic video is a panoramic image comprising pieces of information corresponding respectively to the different positions.

* * * * *